United States Patent
Nishioka et al.

(10) Patent No.: US 10,280,148 B2
(45) Date of Patent: May 7, 2019

(54) ELECTROCONDUCTIVE MEMBER FOR ELECTROPHOTOGRAPHY AND QUATERNARY AMMONIUM SALT

(71) Applicant: CANON KABUSHIKI KAISHA, Tokyo (JP)

(72) Inventors: Satoru Nishioka, Suntou-gun (JP); Satoru Yamada, Numazu (JP); Kazuhiro Yamauchi, Suntou-gun (JP); Yuichi Kikuchi, Susono (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 173 days.

(21) Appl. No.: 15/328,262

(22) PCT Filed: Sep. 4, 2015

(86) PCT No.: PCT/JP2015/075775
§ 371 (c)(1),
(2) Date: Jan. 23, 2017

(87) PCT Pub. No.: WO2016/039431
PCT Pub. Date: Mar. 17, 2016

(65) Prior Publication Data
US 2017/0210719 A1 Jul. 27, 2017

(30) Foreign Application Priority Data

Sep. 10, 2014 (JP) ................................. 2014-184520

(51) Int. Cl.
*G03G 15/02* (2006.01)
*C07D 303/36* (2006.01)
(Continued)

(52) U.S. Cl.
CPC ......... *C07D 303/36* (2013.01); *C07D 471/08* (2013.01); *C07D 487/08* (2013.01);
(Continued)

(58) Field of Classification Search
None
See application file for complete search history.

(56) References Cited

U.S. PATENT DOCUMENTS 6,127,622 A 10/2000 Yamada et al.
8,298,670 B2 10/2012 Muranaka et al.
(Continued)

FOREIGN PATENT DOCUMENTS

JP H05-310818 11/1993
JP 2004-258277 9/2004
(Continued)

OTHER PUBLICATIONS

Pant et al. "Hybrid Siloxane Epoxy Coatings Containing Quaternary Ammonium Moieties" Journal of Applied Polymer Science, 2008, 110, 3080-3086. (Year: 2008).*
(Continued)

*Primary Examiner* — Robert S Loewe
(74) *Attorney, Agent, or Firm* — Venable LLP

(57) ABSTRACT

Provided is an electroconductive member for electrophotography in which movement of a quaternary ammonium salt toward the surface of a binder resin is suppressed and which exhibits a less reduction in electroconductivity through electrification. The electroconductive member for electrophotography comprises an electroconductive shaft core and a resin layer, and the resin layer comprises a binder resin and at least one selected from quaternary ammonium salts having structures represented by the formulae (1) to (8).

15 Claims, 4 Drawing Sheets

(51) Int. Cl.

| | | |
|---|---|---|
| *C08K 5/17* | (2006.01) | |
| *C08K 5/19* | (2006.01) | |
| *C08L 63/00* | (2006.01) | |
| *C08L 101/00* | (2006.01) | |
| *G03G 15/08* | (2006.01) | |
| *G03G 15/16* | (2006.01) | |
| *G03G 21/00* | (2006.01) | |
| *C07D 471/08* | (2006.01) | |
| *C08G 59/24* | (2006.01) | |
| *C08G 59/32* | (2006.01) | |
| *C08G 59/28* | (2006.01) | |
| *C07D 487/08* | (2006.01) | |

(52) U.S. Cl.
CPC .............. *C08G 59/24* (2013.01); *C08G 59/28* (2013.01); *C08G 59/3218* (2013.01); *C08G 59/3227* (2013.01); *C08K 5/17* (2013.01); *C08K 5/19* (2013.01); *C08L 63/00* (2013.01); *C08L 101/00* (2013.01); *G03G 15/02* (2013.01); *G03G 15/0216* (2013.01); *G03G 15/0233* (2013.01); *G03G 15/0808* (2013.01); *G03G 15/0818* (2013.01); *G03G 15/1685* (2013.01); *G03G 21/0017* (2013.01); *C08K 2201/001* (2013.01)

(56) References Cited

U.S. PATENT DOCUMENTS

| | | |
|---|---|---|
| 8,449,975 B2 | 5/2013 | Hirakoso et al. |
| 8,628,854 B2 | 1/2014 | Yamauchi et al. |
| 8,668,987 B2 | 3/2014 | Yamauchi et al. |
| 8,715,830 B2 | 5/2014 | Yamada et al. |
| 8,771,818 B2 | 7/2014 | Nishioka et al. |
| 8,852,743 B2 | 10/2014 | Kikuchi et al. |
| 9,023,465 B2 | 5/2015 | Yamada et al. |
| 9,086,643 B2 | 7/2015 | Kikuchi et al. |
| 9,128,403 B2 | 9/2015 | Yamauchi et al. |
| 9,146,482 B2 | 9/2015 | Watanabe et al. |
| 9,360,789 B1 | 6/2016 | Masu et al. |
| 9,442,408 B2 | 9/2016 | Yamauchi et al. |
| 9,442,451 B2 | 9/2016 | Yamauchi et al. |
| 9,541,854 B2 | 1/2017 | Kikuchi et al. |
| 9,547,250 B2 | 1/2017 | Kikuchi et al. |
| 9,551,949 B2 | 1/2017 | Yamauchi et al. |
| 9,581,931 B2 | 2/2017 | Yamada et al. |
| 2006/0167189 A1 | 7/2006 | Mizuno et al. |
| 2012/0251171 A1 | 10/2012 | Muranaka et al. |
| 2012/0308261 A1 | 12/2012 | Tsuru et al. |
| 2013/0281276 A1 | 10/2013 | Watanabe et al. |
| 2014/0221184 A1 | 8/2014 | Arimura et al. |
| 2014/0287899 A1 | 9/2014 | Nishioka et al. |
| 2015/0093151 A1 | 4/2015 | Muranaka et al. |
| 2015/0198900 A1 | 7/2015 | Yamada et al. |
| 2015/0198907 A1 | 7/2015 | Hino et al. |
| 2015/0331339 A1 | 11/2015 | Yamada et al. |
| 2015/0331340 A1 | 11/2015 | Nishioka et al. |
| 2015/0331341 A1 | 11/2015 | Yamaguchi et al. |
| 2015/0331342 A1 | 11/2015 | Yamaguchi et al. |
| 2015/0331346 A1 | 11/2015 | Yamauchi et al. |
| 2015/0331347 A1 | 11/2015 | Arimura et al. |
| 2016/0054674 A1 | 2/2016 | Muranaka et al. |
| 2016/0154323 A1 | 6/2016 | Nishioka et al. |
| 2016/0187801 A1 | 6/2016 | Yamada et al. |
| 2016/0187809 A1 | 6/2016 | Yamaguchi et al. |
| 2016/0252836 A1 | 9/2016 | Yamada et al. |

FOREIGN PATENT DOCUMENTS

| | | |
|---|---|---|
| JP | 2005-120158 | 5/2005 |
| JP | 2006-189894 | 7/2006 |
| JP | 2010-212689 | 9/2010 |

OTHER PUBLICATIONS

Burness et al. "Synthesis and Reactions of Quaternary Salts of Glycidyl Amines" Journal of Organic Chemistry, 1963, 2283-2288. (Year: 1963).*

* cited by examiner

ELECTROCONDUCTIVE MEMBER FOR ELECTROPHOTOGRAPHY AND QUATERNARY AMMONIUM SALT

TECHNICAL FIELD

The present invention relates to an electroconductive member for electrophotography and a novel quaternary ammonium salt which can be used for the same.

BACKGROUND ART

In general, an electroconductive resin composition is provided with desired electroconductivity through addition of an electroconductive agent to an insulating binder resin. As the electroconductive agent, there have been known an electronic electroconductive agent such as carbon black or metal powder, and an ionic electroconductive agent such as a quaternary ammonium salt.

The ionic electroconductive agent can uniformly provide electroconductivity to the binder resin as compared to the electronic electroconductive agent of a particle dispersion type typified by carbon black, because the ionic electroconductive agent is uniformly dispersed in the binder resin with ease. In addition, the ionic electroconductive agent causes less coloration of the binder resin, and hence can ensure transparency required for, e.g., a packing material or a protective film for display. However, in some cases, the ionic electroconductive agent present in the binder resin moves toward a surface of the binder resin with the lapse of time, that is, so-called bleeding occurs, resulting in a sticky surface or fouling of a member to be brought into contact. In addition, there is a problem in that the ionic electroconductive agent is ionized into an anion component and a cation component through electrification and moves to be unevenly distributed, resulting in a reduction in electroconductivity.

The ionic electroconductive agent has the above-mentioned shortcomings. However, the ionic electroconductive agent is often used for an electroconductive member for electrophotography by virtue of its feature of being capable of uniformly and stably providing electroconductivity of medium-resistance regions with ease, which is difficult to accomplish by the electronic electroconductive agent. As the electroconductive member for electrophotography to which the ionic electroconductive agent provides electroconductivity, there is given, for example, a charging roller which is arranged so as to be brought into abutment with a photosensitive member and is configured to uniformly charge the photosensitive member.

However, as described above, owing to the problem of the ionic electroconductive agent moving toward the surface, fouling with the ionic electroconductive agent may occur in the photosensitive member to be brought into contact with the charging roller, resulting in an image defect. In addition, in recent years, an electrophotographic image forming apparatus has achieved a higher speed and higher definition, and along with this, the image defect is more liable to occur in association with a reduction in electroconductivity of the charging roller.

Against the foregoing problems, in PTL 1, it is disclosed that a quaternary ammonium salt in which, out of four alkyl groups to be bonded to a nitrogen atom of the quaternary ammonium salt, any one of the groups is an octyl group, and the other three groups are methyl groups is used as the ionic electroconductive agent. When such ionic electroconductive agent is used, the ionic electroconductive agent is less liable to move toward the surface by virtue of its polarity being controlled.

In addition, in PTL 2, it is disclosed that a quaternary ammonium salt having a glycidyl group, which is a reactive functional group, is used as the ionic electroconductive agent. Specifically, the glycidyl group of the quaternary ammonium salt reacts with a functional group present in a binder resin, such as a hydroxyl group, a carboxylic acid group, or an amino group, to form a covalent bond. As a result, the quaternary ammonium salt is fixed in the binder resin, and its movement toward the surface is suppressed. In addition, also a reduction in electroconductivity through electrification is suppressed.

CITATION LIST

Patent Literature

PTL 1: Japanese Patent Application Laid-Open No. 2006-189894
PTL 2: Japanese Patent Application Laid-Open No. 2004-258277

SUMMARY OF INVENTION

Technical Problem

Although the ionic electroconductive agent disclosed in PTL 1 is suppressed in bleeding, a rubber is limited to a specific one, and there is a risk of a reduction in electroconductivity through electrification. In addition, the effect disclosed in PTL 2 is exhibited through fixation of the quaternary ammonium salt used as the ionic electroconductive agent in the binder resin. In the case where the quaternary ammonium salt remains, however, the remaining quaternary ammonium salt moves toward the surface of the binder resin or causes a reduction in electroconductivity through electrification with the lapse of time. Therefore, the binder resin which can be used is limited, because the quaternary ammonium salt cannot be fixed unless the number of reactive functional groups present in the binder resin is excessive with respect to the quaternary ammonium salt required for providing desired electroconductivity.

The present invention has been made in view of the foregoing technical background, and an object of the present invention is to provide an electroconductive member for electrophotography in which movement of a quaternary ammonium salt as an ionic electroconductive agent toward the surface of a binder resin is suppressed and which exhibits a less reduction in electroconductivity through electrification. Another object of the present invention is to provide a novel quaternary ammonium salt which can be used for the electroconductive member for electrophotography.

Solution to Problem

According to a first embodiment of the present invention, there is provided an electroconductive member for electrophotography, comprising:
an electroconductive shaft core; and
a resin layer,
wherein the resin layer comprises:
a binder resin; and
at least one selected from quaternary ammonium salts having structures represented by the following formulae (1) to (8):

Formula (1)

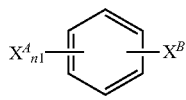

in the formula (1), n1 represents 2 or 3, $X^A$ represents a group having a structure represented by the following formula (9), and $X^B$ represents an electron-donating group or a hydrogen atom;

Formula (9)

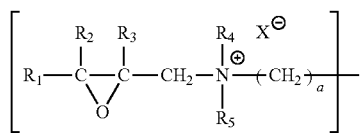

in the formula (9), $R_1$ to $R_3$ each independently represent a hydrogen atom or a methyl group, $R_4$ and $R_5$ each independently represent a methyl group, an ethyl group, or a glycidyl group, $X^-$ represents an anion, and "a" represents 0 or 1;

Formula (2)

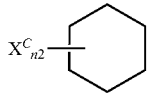

in the formula (2), n2 represents 2 or 3, and $X^C$ represents a group having a structure represented by the following formula (10);

Formula (10)

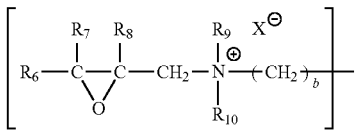

in the formula (10), $R_6$ to $R_8$ each independently represent a hydrogen atom or a methyl group, $R_9$ and $R_{10}$ each independently represent a methyl group, an ethyl group, or a glycidyl group, $X^-$ represents an anion, and "b" represents 0 or 1;

Formula (3)

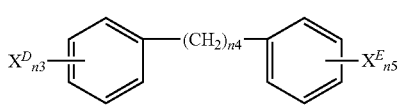

in the formula (3), n3 and n5 each independently represent 1 or 2, n4 represents 1 or 2, and $X^D$ and $X^E$ each independently represent a group having a structure represented by the following formula (11);

Formula (11)

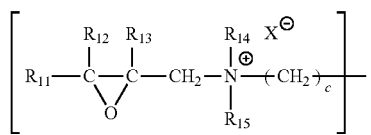

in the formula (11), $R_{11}$ to $R_{13}$ each independently represent a hydrogen atom or a methyl group, $R_{14}$ and $R_{15}$ each independently represent a methyl group, an ethyl group, or a glycidyl group, $X^-$ represents an anion, and "c" represents 0 or 1;

Formula (4)

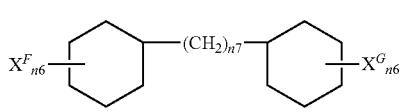

in the formula (4), n6 and n8 each independently represent 1 or 2, n7 represents 1 or 2, and $X^F$ and $X^G$ each independently represent a group having a structure represented by the following formula (12);

Formula (12)

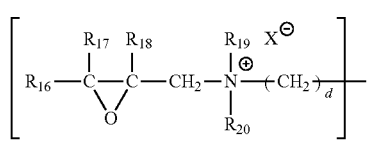

in the formula (12), $R_{16}$ to $R_{18}$ each independently represent a hydrogen atom or a methyl group, $R_{19}$ and $R_{20}$ each independently represent a methyl group, an ethyl group, or a glycidyl group, $X^-$ represents an anion, and "d" represents 0 or 1;

Formula (5)

in the formula (5), "e" represents 1 or 2, and $X^H$ and $X^I$ each independently represent a group having a structure represented by the following formula (13);

Formula (13)

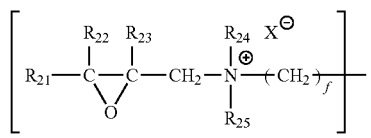

in the formula (13), $R_{21}$ to $R_{23}$ each independently represent a hydrogen atom or a methyl group, $R_{24}$ and $R_{25}$ each independently represent a methyl group, an ethyl group, or a glycidyl group, $X^-$ represents an anion, and "f" represents 2 or 3;

Formula (6)

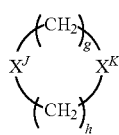

in the formula (6), "g" and "h" each independently represent 2 or 3, and $X^J$ and $X^K$ each independently represent a group having a structure represented by the following formula (14);

Formula (14)

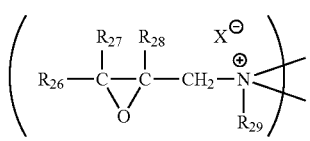

in the formula (14), $R_{26}$ to $R_{28}$ each independently represent a hydrogen atom or a methyl group, $R_{29}$ represents a methyl group, an ethyl group, or a glycidyl group, and $X^-$ represents an anion;

Formula (7)

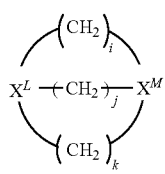

in the formula (7), "i", "j", and "k" each independently represent 2 or 3, and $X^L$ and $X^M$ each independently represent a group having a structure represented by the following formula (15);

Formula (15)

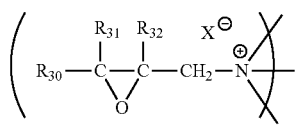

in the formula (15), $R_{30}$ to $R_{32}$ each independently represent a hydrogen atom or a methyl group, and $X^-$ represents an anion;

Formula (8)

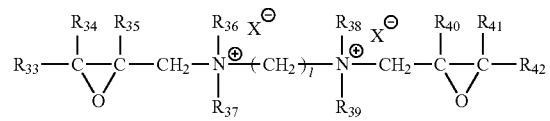

in the formula (8), $R_{33}$ to $R_{35}$ and $R_{40}$ to $R_{42}$ each independently represent a hydrogen atom or a methyl group, $R_{36}$ to $R_{39}$ each independently represent a methyl group, an ethyl group, or a glycidyl group, "l" represents an integer of 2 or more and 12 or less, and $X^-$ represents an anion.

According to a second embodiment of the present invention, there is provided an electroconductive member for electrophotography, comprising:
an electroconductive shaft core; and
a resin layer,
wherein the resin layer comprises:
at least one selected from quaternary ammonium salts having structures represented by the formulae (1) to (8); and
a binder resin obtained from a compound having two or more functional groups selected from a hydroxyl group, a mercapto group, an amino group, and an acid anhydride group.

Further, according to a third embodiment of the present invention, there is provided a quaternary ammonium salt having a structure represented by any one of the following formulae (1) to (5):

Formula (1)

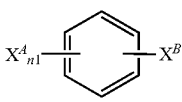

in the formula (1), n1 represents 2 or 3, $X^A$ represents a group having a structure represented by the following formula (9), and $X^B$ represents an electron-donating group or a hydrogen atom;

Formula (9)

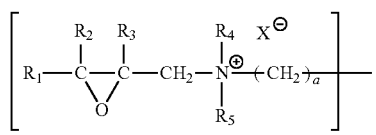

in the formula (9), $R_1$ to $R_3$ each independently represent a hydrogen atom or a methyl group, $R_4$ and $R_5$ each independently represent a methyl group, an ethyl group, or a glycidyl group, $X^-$ represents an anion, and "a" represents 0 or 1;

Formula (2)

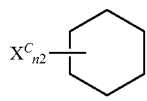

in the formula (2), n2 represents 2 or 3, and $X^C$ represents a group having a structure represented by the following formula (10);

Formula (10)

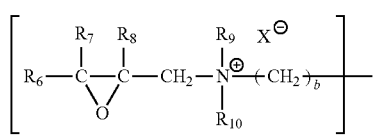

in the formula (10), $R_6$ to $R_8$ each independently represent a hydrogen atom or a methyl group, $R_9$ and $R_{10}$ each independently represent a methyl group, an ethyl group, or a glycidyl group, $X^-$ represents an anion, and "b" represents 0 or 1;

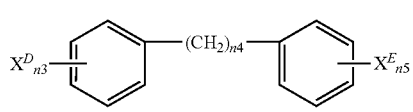

Formula (3)

in the formula (3), n3 and n5 each independently represent 1 or 2, n4 represents 1 or 2, and $X^D$ and $X^E$ each independently represent a group having a structure represented by the following formula (11);

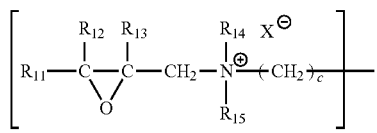

Formula (11)

in the formula (11), $R_{11}$ to $R_{13}$ each independently represent a hydrogen atom or a methyl group, $R_{14}$ and $R_{15}$ each independently represent a methyl group, an ethyl group, or a glycidyl group, $X^-$ represents an anion, and "c" represents 0 or 1;

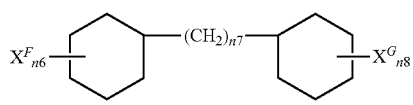

Formula (4)

in the formula (4), n6 and n8 each independently represent 1 or 2, n7 represents 1 or 2, and $X^F$ and $X^G$ each independently represent a group having a structure represented by the following formula (12);

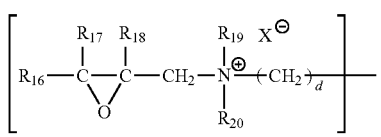

Formula (12)

in the formula (12), $R_{16}$ to $R_{18}$ each independently represent a hydrogen atom or a methyl group, $R_{19}$ and $R_{20}$ each independently represent a methyl group, an ethyl group, or a glycidyl group, $X^-$ represents an anion, and "d" represents 0 or 1;

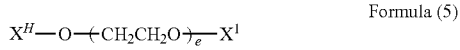

Formula (5)

in the formula (5), "e" represents 1 or 2, and $X^H$ and $X^I$ each independently represent a group having a structure represented by the following formula (13);

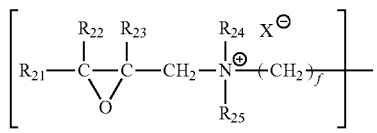

Formula (13)

in the formula (13), $R_{21}$ to $R_{23}$ each independently represent a hydrogen atom or a methyl group, $R_{24}$ and $R_{25}$ each independently represent a methyl group, an ethyl group, or a glycidyl group, $X^-$ represents an anion, and "f" represents 2 or 3.

Advantageous Effects of Invention

According to the embodiments of the present invention, movement of the quaternary ammonium salt as an ionic electroconductive agent toward the surface of the binder resin and a reduction in electroconductivity through electrification are suppressed. Further, when the quaternary ammonium salt according to the present invention is used as an ionic electroconductive agent, the electroconductive member for electrophotography to be obtained can realize less occurrence of fouling of a photosensitive member and less occurrence of an image defect even through continuous output of a high-definition image at a high speed.

In addition, according to the embodiment of the present invention, the novel quaternary ammonium salt to be obtained can provide an electroconductive member for electrophotography contributing to formation of an electrophotographic image of high quality.

Further features of the present invention will become apparent from the following description of exemplary embodiments with reference to the attached drawings.

DESCRIPTION OF EMBODIMENTS

Figure 1A:
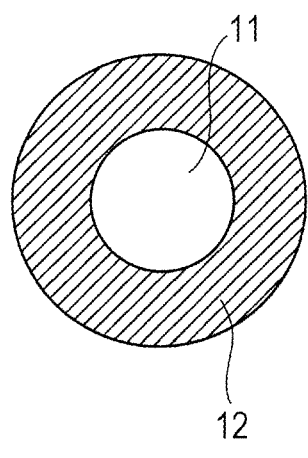
FIG. 1A is a schematic view of a charging roller, which is an electroconductive member for electrophotography according to one embodiment of the present invention.

Preferred embodiments of the present invention will now be described in detail in accordance with the accompanying drawings.

The inventors of the present invention have focused attention on the compatibility of a quaternary ammonium salt with a binder resin, and the movement and diffusion of the quaternary ammonium salt at the time when the electrification is performed and when the electrification is not performed.

The movement of the quaternary ammonium salt toward the surface of the binder resin with the lapse of time is associated with the compatibility of the quaternary ammonium salt with the binder resin. In general, the quaternary ammonium salt is dissolved in water well. This is because the quaternary ammonium salt is reduced in charge density through electron donation from an unshared electron pair on an oxygen atom in a water molecule and hence can exist stably. However, many binder resins cannot donate an electron to the quaternary ammonium salt. Therefore, the quaternary ammonium salt easily moves toward the surface of the binder resin, in which the quaternary ammonium salt can be brought into contact with a water content in the air.

In view of the foregoing, the inventors have made an attempt to reduce the charge density on a nitrogen atom in the molecule of the quaternary ammonium salt by introducing a chemical structure having an electron donating property in the molecule. As a result, the movement of the quaternary ammonium salt toward the surface of the binder resin was able to be suppressed.

As the chemical structure capable of donating an electron, an ether group or an aromatic ring has been known.

The ether group has a structure in which hydrogen atoms in a water molecule are transformed to alkyl groups, and can donate an electron from an unshared electron pair on an oxygen atom. It has been known that, of the ether groups, an ether group having an ethylene oxide structure (hereinafter also referred to as "ethylene oxide structure") is particularly effective in stabilizing the quaternary ammonium salt. Other than the ethylene oxide structure, also an ether group having a cyclic ether structure is considered to have a large stabilization effect on the quaternary ammonium salt. The reason for this is that an alkyl chain constituting the ether group has small steric hindrance, and hence the quaternary ammonium salt relatively easily exists in the vicinity of an oxygen atom. Of the ether groups each having a cyclic ether structure, a glycidyl group is particularly preferred, because the glycidyl group can react with a functional group in the binder resin and enables fixation, in addition to enabling stabilization of the quaternary ammonium salt through electron donation. It should be noted that, in order to stabilize the quaternary ammonium salt through electron donation, the ether group and the quaternary ammonium salt preferably exist so as to be as close as possible to each other.

The aromatic ring is a compound having a conjugated unsaturated cyclic structure satisfying Huckel's rule, typified by a benzene ring. The aromatic ring has an electron donating property by virtue of the conjugated unsaturated cyclic structure realizing delocalization of charge (mesomeric effect). Further, an aromatic ring on which an electron-donating functional group, such as a hydroxyl group or a methoxy group, exists is preferred by virtue of a higher electron donating property.

In actuality, a quaternary ammonium salt in which a glycidyl group, which was one kind of the ether groups, was introduced, and further, the ethylene oxide structure and the aromatic ring were introduced was used and its compatibility with the binder resin was investigated. As a result, its movement toward the surface with the lapse of time was suppressed.

Next, with regard to a reduction in electroconductivity through electrification, the following is considered to be associated therewith: an anion component and a cation component constituting the quaternary ammonium salt are unevenly distributed; and it takes a long time to pair these components from the unevenly distributed state. That is, in the case where the components of the quaternary ammonium salt are hard to move at the time when the electrification is performed, the reduction in electroconductivity through electrification can be suppressed. However, when the movement of the components of the quaternary ammonium salt is merely suppressed, its electroconductivity providing ability is reduced.

Against the problem in that, when the components of the quaternary ammonium salt are hard to move, its electroconductivity providing ability is reduced, while the reduction in electroconductivity through electrification can be suppressed, the inventors of the present invention have considered as described below. Specifically, the inventors have considered that, when the molecule of the quaternary ammonium salt is designed to suppress the movement of its cation component at the time when the electrification is performed and facilitate the movement of the cation component at the time when the electrification is not performed, such quaternary ammonium salt exhibits a high electroconductivity providing ability and the reduction in electroconductivity can be well suppressed through electrification.

The anion component of the quaternary ammonium salt is generally considered to move faster than the cation component of the quaternary ammonium salt does at the time when the electrification is performed because of having a lower molecular weight. The inventors have considered that the foregoing is achieved by: exhibiting electroconductivity by the anion component moving faster; and shortening the time for pairing of the components by designing the molecule to suppress the movement of the cation component at the time when the electrification is performed, shorten the distance between the anion component and the cation component, and facilitate movement of the cation component at the time when the electrification is not performed.

The inventors have made various investigations and have found that the reduction in electroconductivity through electrification is suppressed by an ionic electroconductive agent having a quaternary ammonium salt structure in a rigid structure, such as an aromatic ring or an alicyclic hydrocarbon, or having the quaternary ammonium salt structure in the vicinity of both ends of a long-chain structure, such as an alkyl chain or an ethylene oxide structure.

The mechanism is not clearly understood, but is presumed as described below.

At the time when the electrification is performed, the cation component of the quaternary ammonium salt is considered to move to the vicinity of a nitrogen atom of the quaternary ammonium salt by a Coulomb force generated on the nitrogen atom of the quaternary ammonium salt positively charged.

It is assumed that the structure of the quaternary ammonium salt exists in the vicinity of both ends of the rigid cyclic structure or the long-chain structure. For example, a quaternary ammonium salt having the cyclic structure is considered to form a rod-like compound by the rigidity. In addition, also a quaternary ammonium salt having the long-chain structure is considered to have a linear form, because quaternary ammonium salt structures existing in the vicinity of both the ends of the long-chain structure causes electrostatic repulsion and move away from each other as much as possible. When such compounds move through electrification, the compounds move by the Coulomb force generated in the quaternary ammonium salts, and hence the quaternary ammonium salts are considered to move so that the longitudinal directions of the compounds are perpendicular to their movement directions.

Accordingly, the quaternary ammonium salt inevitably moves while being entwined with a polymer chain or a cross-linking network of the binder resin. As a result, at the time when the electrification is performed, the quaternary ammonium salt moves slowly. However, at the time when the electrification is not performed, the Coulomb force generated in the quaternary ammonium salt disappears and the quaternary ammonium salt can move freely. In consequence, the quaternary ammonium salt can move in a state of easily passing through the polymer chain or cross-linking network of the binder resin. Accordingly, the cation component at the time when the electrification is not performed moves faster than the component does at the time when the electrification is performed, and can quickly pair up with the anion component, which is another component constituting the quaternary ammonium salt. It is considered that the feature of moving slowly at the time when the electrification is performed and diffusing rapidly at the time when the electrification is not performed causes a suppressing effect on the reduction in electroconductivity through electrification.

It should be noted that, when the quaternary ammonium salt has the aromatic ring as the rigid cyclic structure or the ethylene oxide structure as the long-chain structure, a high suppressing effect on the movement of the quaternary ammonium salt toward the surface of the resin is obtained.

Further, when the quaternary ammonium salt has a plurality of epoxy groups or glycidyl groups, which are reactive functional groups, such the groups react with a hydroxyl group or a carboxylic acid group of the binder resin to form a covalent bond, and hence the quaternary ammonium salt can also be fixed in the binder resin. As a result, the movement of the quaternary ammonium salt toward the surface of the binder resin and the reduction in electroconductivity through electrification can be more suppressed.

A quaternary ammonium salt according to an embodiment of the present invention is described in detail below.

The quaternary ammonium salt according to the present invention has a structure represented by any one of the following formulae (1) to (5).

It should be noted that $X^-$ represents a counter anion of the quaternary ammonium salt in each of the following formulae (1) to (5). A counter anion appropriately selected from those known in the field of an ionic electroconductive agent may be used.

Examples of the counter anion include a halide ion such as a fluorine ion, a chlorine ion, a bromine ion, or an iodine ion, a perchlorate ion, and a bis(trifluoromethane)sulfonimide anion.

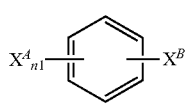

Formula (1)

(In the formula (1), n1 represents 2 or 3, $X^A$ represents a group having a structure represented by the following formula (9), and $X^B$ represents an electron-donating group or a hydrogen atom.)

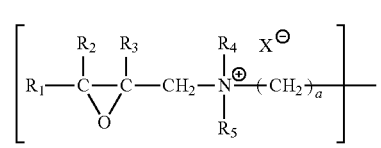

Formula (9)

(In the formula (9), $R_1$ to $R_3$ each independently represent a hydrogen atom or a methyl group, $R_4$ and $R_5$ each independently represent a methyl group, an ethyl group, or a glycidyl group, $X^-$ represents an anion, and "a" represents 0 or 1.)

When two or more $X^A$'s exist in the formula (1), the reduction in electroconductivity through electrification can be suppressed.

In contrast, when four or more $X^A$'s exist in the formula (1), steric hindrance becomes large, and the synthesis of the quaternary ammonium salt becomes difficult.

When $X^B$ as an electron-donating group exists, a benzene ring has a higher electron donating property, and alleviates the positive charge of the quaternary ammonium salt. As a result, the quaternary ammonium salt exhibits higher compatibility with a binder resin in association with a reduction in its polarity, and its movement toward the surface of the resin is reduced. When $X^B$ as an electron-donating group is a hydroxyl group, a methoxy group, or a methyl group, the compound represented by the formula (1) is easily synthesized because a reduction in reactivity caused by the bulkiness of a functional group can be suppressed. When $R_1$ to $R_3$ in the formula (9) representing the structure of $X^A$ each represent a hydrogen atom or a methyl group, steric hindrance becomes small, and hence an electron is easily donated to the quaternary ammonium salt. When $R_4$ and $R_5$ each represent a methyl group, an ethyl group, or a glycidyl group, a tertiary amine is easily transformed to the quaternary ammonium salt through functional group transformation. In addition, when "a" represents 0, an electron can be donated from the benzene ring, and when "a" represents 1, the tertiary amine is easily transformed to the quaternary ammonium salt through functional group transformation by virtue of high reactivity as compared to the case where "a" represents 0, and a rigid rod-like structure can be maintained.

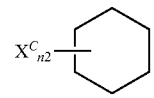

Formula (2)

(In the formula (2), n2 represents 2 or 3, $X^C$ represents a group having a structure represented by the following formula (10).)

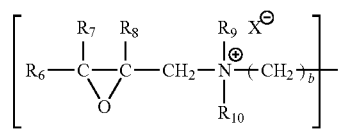

Formula (10)

(In the formula (10), $R_6$ to $R_8$ each independently represent a hydrogen atom or a methyl group, $R_9$ and $R_{10}$ each independently represent a methyl group, an ethyl group, or a glycidyl group, X⁻ represents an anion, and "b" represents 0 or 1.)

When two or more $X^C$'s exist in the formula (2), the reduction in electroconductivity through electrification can be suppressed.

In contrast, when four or more $X^C$'s exist in the formula (2), steric hindrance becomes large, and the synthesis of the quaternary ammonium salt becomes difficult.

When $R_6$ to $R_8$ in the formula (10) representing the structure of $X^C$ each represent a hydrogen atom or a methyl group, steric hindrance becomes small, and hence an electron is easily donated to the quaternary ammonium salt, and in addition, the quaternary ammonium salt is easily fixed in the binder resin through a reaction with the functional group of the binder resin. When $R_9$ and $R_{10}$ each represent a methyl group, an ethyl group, or a glycidyl group, a tertiary amine is easily transformed to the quaternary ammonium salt through functional group transformation. In addition, when "b" represents 0 or 1, the quaternary ammonium salt forms a rigid rod-like compound, and hence the reduction in electroconductivity through electrification can be suppressed.

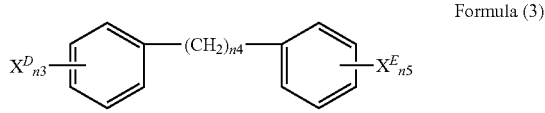

Formula (3)

(In the formula (3), n3 and n5 each independently represent 1 or 2, n4 represents 1 or 2, and $X^D$ and $X^E$ each independently represent a group having a structure represented by the following formula (11).)

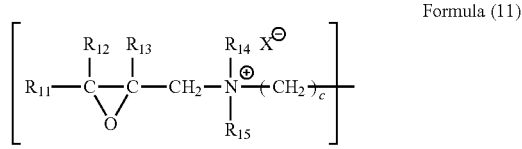

Formula (11)

(In the formula (11), $R_{11}$ to $R_{13}$ each independently represent a hydrogen atom or a methyl group, $R_{14}$ and $R_{15}$ each independently represent a methyl group, an ethyl group, or a glycidyl group, X⁻ represents an anion, and "c" represents 0 or 1.)

When three or more $X^D$'s or $X^E$'s exist in the formula (3), steric hindrance becomes large, and the synthesis of the quaternary ammonium salt becomes difficult.

When n4 represents 2 or less, the quaternary ammonium salt forms a rigid rod-like compound, and the reduction in electroconductivity through electrification can be suppressed. When $R_{11}$ to $R_{13}$ in the formula (11) representing the structures of $X^D$ and $X^E$ each represent a hydrogen atom or a methyl group, steric hindrance becomes small, and hence an electron is easily donated to the quaternary ammonium salt, and in addition, the quaternary ammonium salt is easily fixed in the binder resin through a reaction with the functional group of the binder resin. When $R_{14}$ and $R_{15}$ each represent a methyl group, an ethyl group, or a glycidyl group, a tertiary amine is easily transformed to the quaternary ammonium salt through functional group transformation. In addition, when "c" represents 0, an electron can be donated from a benzene ring, and when "c" represents 1, the tertiary amine is easily transformed to the quaternary ammonium salt through functional group transformation by virtue of high reactivity as compared to the case where "c" represents 0, and the rigid rod-like compound can be maintained.

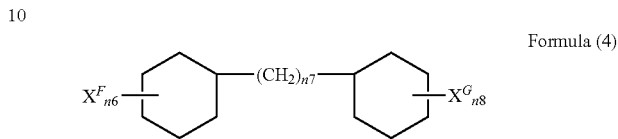

Formula (4)

(In the formula (4), n6 and n8 each independently represent 1 or 2, n7 represents 1 or 2, and $X^F$ and $X^G$ each independently represent a group having a structure represented by the following formula (12).)

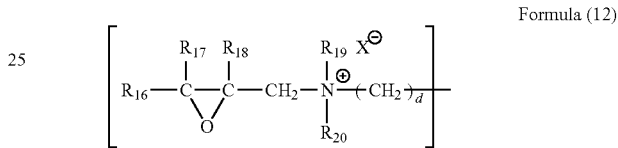

Formula (12)

(In the formula (12), $R_{16}$ to $R_{18}$ each independently represent a hydrogen atom or a methyl group, $R_{19}$ and $R_{20}$ each independently represent a methyl group, an ethyl group, or a glycidyl group, X⁻ represents an anion, and "d" represents 0 or 1.)

When three or more $X^F$'s or $X^G$'s exist in the formula (4), steric hindrance becomes large, and the synthesis of the quaternary ammonium salt becomes difficult. When n7 represents 2 or less, the quaternary ammonium salt forms a rigid rod-like compound, and hence the reduction in electroconductivity through electrification can be suppressed. When $R_{16}$ to $R_{18}$ in the formula (12) representing the structures of $X^F$ and $X^G$ each represent a hydrogen atom or a methyl group, steric hindrance becomes small, and hence an electron is easily donated to the quaternary ammonium salt, and in addition, the quaternary ammonium salt is easily fixed in the binder resin through a reaction with the functional group of the binder resin. When $R_{19}$ and $R_{20}$ each represent a methyl group, an ethyl group, or a glycidyl group, a tertiary amine is easily transformed to the quaternary ammonium salt through functional group transformation. In addition, when "d" represents 0 or 1, the quaternary ammonium salt forms a rigid rod-like compound, and hence the reduction in electroconductivity through electrification can be suppressed.

Formula (5)

(In the formula (5), "e" represents 1 or 2, and $X^H$ and $X^I$ each independently represent a group having a structure represented by the following formula (13).)

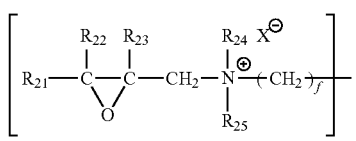

Formula (13)

(In the formula (13), $R_{21}$ to $R_{23}$ each independently represent a hydrogen atom or a methyl group, $R_{24}$ and $R_{25}$ each independently represent a methyl group, an ethyl group, or a glycidyl group, $X^-$ represents an anion, and "f" represents 2 or 3.)

When "e" represents 1 or 2 in the formula (5), an electron can be donated from an ethylene oxide structure to the quaternary ammonium salt, and in addition, a moderate suppressing effect on a moving speed is obtained at the time when the electrification is performed. In addition, when "e" becomes larger, moisture absorption occurs in a high-temperature and high-humidity environment owing to the hydrophilicity of the ethylene oxide structure, which causes a reduction in resistance. $R_{21}$ to $R_{23}$ in the formula (13) representing the structures of $X^H$ and $X^I$ each represent a hydrogen atom or a methyl group, steric hindrance becomes small, and hence an electron is easily donated to the quaternary ammonium salt, and in addition, the quaternary ammonium salt is easily fixed in the binder resin through a reaction with the functional group of the binder resin. When $R_{24}$ and $R_{25}$ each represent a methyl group, an ethyl group, or a glycidyl group, a tertiary amine is easily transformed to the quaternary ammonium salt through functional group transformation.

In addition, when "f" represents 2 or 3, the quaternary ammonium salt can be easily synthesized by virtue of high reactivity.

Also quaternary ammonium salts having structures represented by the following formulae (6) to (8) are used for an electroconductive member for electrophotography according to the present invention, as with the quaternary ammonium salt having a structure represented by any one of the formulae (1) to (5). It should be noted that $X^-$ represents a counter anion of the quaternary ammonium salt in the following formula (8). A counter anion appropriately selected from those known in the field of an ionic electroconductive agent may be used. Examples of the counter anion include a halide ion, such as a fluorine ion, a chlorine ion, a bromine ion, or an iodine ion, a perchlorate ion, and a bis(trifluoromethane)sulfonimide anion.

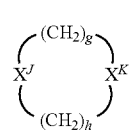

Formula (6)

(In the formula (6), "g" and "h" each independently represent 2 or 3, and $X^J$ and $X^K$ each independently represent a group having a structure represented by the following formula (14).)

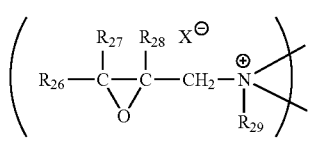

Formula (14)

(In the formula (14), $R_{26}$ to $R_{28}$ each independently represent a hydrogen atom or a methyl group, $R_{29}$ represents a methyl group, an ethyl group, or a glycidyl group, and $X^-$ represents an anion.)

When "g" and "h" each represent 2 or 3 in the formula (6), a tertiary amine is easily transformed to the quaternary ammonium salt through functional group transformation by virtue of high reactivity. When $R_{26}$ to $R_{28}$ in the formula (14) representing the structures of $X^J$ and $X^K$ each represent a hydrogen atom or a methyl group, steric hindrance becomes small, and hence an electron is easily donated to the quaternary ammonium salt, and in addition, the quaternary ammonium salt is easily fixed in the binder resin through a reaction with the functional group of the binder resin. When $R_{29}$ represents a methyl group, an ethyl group, or a glycidyl group, the tertiary amine is easily transformed to the quaternary ammonium salt through functional group transformation.

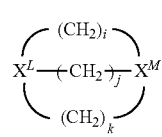

Formula (7)

(In the formula (7), "i", "j", and "k" each independently represent 2 or 3, and $X^L$ and $X^M$ each independently represent a group having a structure represented by the following formula (15).)

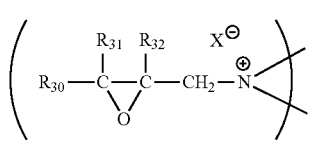

Formula (15)

(In the formula (15), $R_{30}$ to $R_{32}$ each independently represent a hydrogen atom or a methyl group, and $X^-$ represents an anion.)

When "i", "j", and "k" each represent 2 or 3 in the formula (7), a tertiary amine is easily transformed to the quaternary ammonium salt through functional group transformation by virtue of high reactivity. When $R_{30}$ to $R_{32}$ in the formula (15) representing the structures of $X^L$ and $X^M$ each represent a hydrogen atom or a methyl group, steric hindrance becomes small, and hence an electron is easily donated to the quaternary ammonium salt, and in addition, the quaternary ammonium salt is easily fixed in the binder resin through a reaction with the functional group of the binder resin.

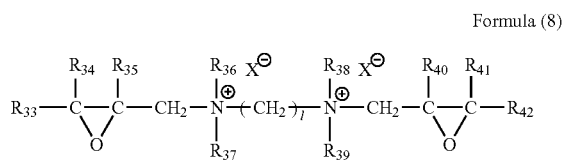

Formula (8)

(In the formula (8), "l" represents an integer of 2 or more and 12 or less, $R_{33}$ to $R_{35}$ and $R_{40}$ to $R_{42}$ each independently represent a hydrogen atom or a methyl group, $R_{36}$ to $R_{39}$ each independently represent a methyl group, an ethyl group, or a glycidyl group, and $X^-$ represents an anion.)

When "l" represents an integer of 2 or more and 12 or less, a moderate suppressing effect on a moving speed is obtained at the time when the electrification is performed, and in addition, a raw material is easily available. When $R_{33}$ to $R_{35}$ and $R_{40}$ to $R_{42}$ each represent a hydrogen atom or a methyl group, steric hindrance becomes small, and hence an electron is easily donated to the quaternary ammonium salt, and in addition, the quaternary ammonium salt is easily fixed in the binder resin through a reaction with the functional group of the binder resin. When $R_{36}$ to $R_{39}$ each represent a methyl group, an ethyl group, or a glycidyl group, a tertiary amine is easily transformed to the quaternary ammonium salt through functional group transformation.

<Synthesis Method for Quaternary Ammonium Salt>

The quaternary ammonium salt according to the present invention may be produced by, for example, the following method using (i) a tertiary amine compound as a raw material and (ii) an amine quaternizing agent as a raw material.

(i) Tertiary Amine as Raw Material

The amine as a raw material is a polyamine compound having a cyclic structure or a long chain. Examples of the cyclic structure include an aromatic ring, such as a benzene ring, and an alicyclic hydrocarbon, such as a cyclohexane ring. Examples of the long chain include an alkyl chain and an ethylene oxide structure. Those amines may be available as reagents.

In the case where those amines are not available, the target polyamine may be produced by using a known reaction of transforming another functional group to an amino group.

As a reaction of introducing an amino group, the following reactions are well known: a nucleophilic substitution reaction of a nitrogen compound with a leaving group, typified by the Gabriel amine synthesis; a reductive amination reaction of transforming a carbonyl group, such as an aldehyde or a ketone, to an amine through functional group transformation; reduction of an amide group, a nitrile group, or a nitro group; the Mannich reaction which is a three-component reaction among formaldehyde, an amine, and carbonyl compound having a hydrogen atom at α position or phenol; and the like.

(ii) Quaternizing Agent as Raw Material

Examples of the quaternizing agent include an alkyl halide compound, such as bromomethane or iodomethane, and an alkyl compound having a tosyl group (p-toluenesulfonyl group) or a mesyl group (methanesulfonyl group). Of those, an epihalohydrin typified by epichlorohydrin, which can introduce an epoxy group simultaneously with functional group transformation of the tertiary amine to the quaternary ammonium salt, is preferred as the quaternizing agent. Those quaternizing agents may be available as reagents. In the case where those quaternizing agents are not available, the target quaternizing agent may be produced by using a known reaction of transforming another functional group to a halogen, a tosyl group, or a mesyl group.

As a reaction of introducing a halogen atom, a tosyl group, or a mesyl group to an alkyl compound, the following reaction is well known: a substitution reaction proceeding through a reaction of an alcohol compound with thionyl chloride, sulfuryl chloride, phosphorus tribromide, p-toluenesulfonyl chloride, methanesulfonyl chloride, or the like.

The quaternary ammonium salt according to the present invention may be produced through a reaction between the tertiary amine and amine quaternizing agent as raw materials thus produced. It should be noted that, in purification of the quaternary ammonium salt, the quaternizing agent is desirably added in excess to the tertiary amine in view of easy removal of the raw materials at a low boiling point. In addition, the reaction may be performed without a solvent or in a solvent. The solvent is preferably a polar solvent capable of dissolving the quaternary ammonium salt, such as an alcohol solvent such as ethanol or isopropyl alcohol, or a halogen-based solvent such as chloroform or dichloromethane.

Next, an electroconductive member for electrophotography according to the present invention is described. An electroconductive member for electrophotography according to an embodiment of the present invention includes an electroconductive shaft core and a resin layer, and the resin layer comprises a binder resin and at least one selected from the quaternary ammonium salts having structures represented by the formulae (1) to (8). An electroconductive member for electrophotography according to an embodiment of the present invention includes an electroconductive shaft core and a resin layer, and the resin layer comprises at least one selected from the quaternary ammonium salts having structures represented by the formulae (1) to (8), and a binder resin obtained from a compound having two or more functional groups selected from a hydroxyl group, a mercapto group, an amino group, and an acid anhydride group.

Figure 1B:
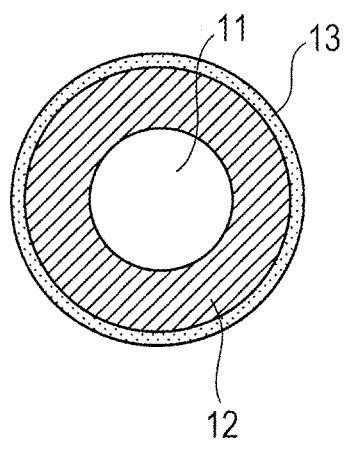
FIG. 1B is a schematic view of the charging roller, which is the electroconductive member for electrophotography according to one embodiment of the present invention.
Figure 1C:
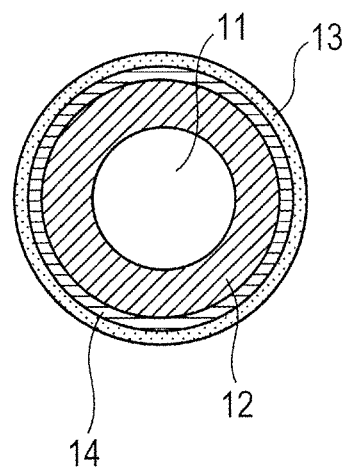
FIG. 1C is a schematic view of the charging roller, which is the electroconductive member for electrophotography according to one embodiment of the present invention.

It should be noted that, while a charging roller is described in detail below as an example of the electroconductive member for electrophotography, the application of the present invention is not limited to the charging roller. All members in an electrophotographic image forming apparatus that require electroconductivity, such as a developing member, a transferring member, and a cleaning member, are encompassed. The charging roller according to the present invention includes an electroconductive shaft core and a resin layer. More specifically, schematic views of the charging roller according to the present invention are illustrated in FIG. 1A to FIG. 1C. As illustrated in FIG. 1A, an elastic layer 12 is formed on the outer periphery of an electroconductive shaft core 11. As illustrated in FIG. 1B, a surface layer 13 may be further formed on the outer periphery of the elastic layer 12. As illustrated in FIG. 1C, a three-layer structure in which an intermediate layer 14 is arranged between the elastic layer 12 and the surface layer 13, or a multilayer structure in which the plurality of intermediate layers 14 are arranged may be adopted.

It should be noted that the elastic layer 12, the intermediate layer 14, and the surface layer 13 are resin layers, and any one or more of the layers comprise the quaternary ammonium salt of the present invention.

<Electroconductive Shaft Core>

An electroconductive shaft core appropriately selected from those known in the field of an electroconductive member for electrophotography may be used as the electroconductive shaft core.

<Resin Layer>
Elastic Layer

A binder resin for forming the elastic layer 12 is not particularly limited, and a binder resin known in the field of an electroconductive member for electrophotography may be used. Examples of such binder resin include a resin, a rubber, and a thermoplastic elastomer.

Examples of the resin include polyolefin-based resins such as polyethylene and polypropylene, polystyrene, polyvinyl alcohol, an ethylene-vinyl alcohol copolymer, a polyacetal resin, a styrene-maleic anhydride copolymer, a copolymer of an olefin such as ethylene or propylene and maleic anhydride, a phenol resin, a melamine resin, an epoxy resin, a polyamide resin, an acrylic resin, and a polyester resin. Polyvinyl alcohol, an ethylene-vinyl alcohol copolymer, or an epoxy resin is particularly preferred from the viewpoint that excellent electroconductivity is obtained when the quaternary ammonium salt is added.

Examples of the rubber include an ethylene-propylene-diene copolymer, a styrene-butadiene copolymerized rubber (SBR), a silicone rubber, an isoprene rubber (IR), a butyl rubber (BR), a chloroprene rubber (CR), an epichlorohydrin homopolymer, an epichlorohydrin-ethylene oxide copolymer, an epichlorohydrin-ethylene oxide-allyl glycidyl ether terpolymer, an acrylonitrile-butadiene copolymer, a hydrogenated product of an acrylonitrile-butadiene copolymer, a carboxylated acrylonitrile-butadiene copolymer such as an acrylonitrile-butadiene-methacrylic acid copolymer, an acrylic rubber, and a urethane rubber.

The following polymers is particularly preferred from the viewpoint that excellent electroconductivity is obtained when the quaternary ammonium salt is added: an epichlorohydrin homopolymer, an epichlorohydrin-ethylene oxide copolymer, an epichlorohydrin-ethylene oxide-allyl glycidyl ether terpolymer, an acrylonitrile-butadiene copolymer, a hydrogenated product of an acrylonitrile-butadiene copolymer, a carboxylated acrylonitrile-butadiene copolymer such as an acrylonitrile-butadiene-methacrylic acid copolymer, an acrylic rubber, and a urethane rubber.

Examples of the thermoplastic elastomer include a urethane-based thermoplastic elastomer, a polystyrene-based thermoplastic elastomer, a fluorine rubber-based thermoplastic elastomer, a polyester-based thermoplastic elastomer, a polyamide-based thermoplastic elastomer, a polybutadiene-based thermoplastic elastomer, an ethylene-vinyl acetate-based thermoplastic elastomer, a polyvinyl chloride-based thermoplastic elastomer, and a chlorinated polyethylene-based thermoplastic elastomer.

A urethane-based thermoplastic elastomer, a polyester-based thermoplastic elastomer, or a polyamide-based thermoplastic elastomer is particularly preferred from the viewpoint that excellent electroconductivity is obtained when the quaternary ammonium salt is added.

A filler, a softener, a processing aid, a tackifier, an anti-tack agent, a dispersant, a blowing agent, or the like, which is generally used as a blending agent for the binder resin, may be added to such elastic layer as long as the effect of the electroconductive member for electrophotography of the present invention is not impaired.

In addition, the following electroconductive agents may appropriately be added as required in order to control the electroconductivity of the elastic layer: carbon black, graphite, a metal oxide having electroconductivity such as tin oxide, metals such as copper and silver, and electroconductive particles each of which has imparted thereto electroconductivity through the coverage of its surface with the oxide or the metal.

Intermediate Layer

A material appropriately selected from those known in the field of an electroconductive member for electrophotography may be used for the intermediate layer 14. Specifically, the materials exemplified in the "Elastic Layer" section may be used.

Surface Layer

A binder resin known in the field of an electroconductive member for electrophotography may be used for the surface layer 13. Specific examples thereof include an acrylic resin, polyurethane, polyamide, polyester, polyolefin, and a silicone resin. In the binder resin for forming the surface layer, there may be used, as needed, an electroconductive agent such as carbon black, graphite, an oxide having electroconductivity such as tin oxide, a metal such as copper or silver, or an electroconductive particle which has imparted thereto electroconductivity through the coverage of its surface with the oxide or the metal.

It should be noted that any one or more of the elastic layer 12, the intermediate layer 14, and the surface layer 13 are formed of a binder resin layer comprising the quaternary ammonium salt according to the present invention. It is particularly preferred to use a binder resin obtained from a compound having two or more functional groups selected from a hydroxyl group, a mercapto group, an amino group, and an acid anhydride group for the resin layer.

Such binder resin can fix the quaternary ammonium salt according to the present invention therein by virtue of having a functional group which reacts with an epoxy group to form a covalent bond in the molecule of the resin. Therefore, the movement of the quaternary ammonium salt toward the surface and the reduction in electroconductivity through electrification can be further suppressed. A binder resin obtained from a compound having an ethylene oxide structure, and two or more functional groups selected from a hydroxyl group, a mercapto group, an amino group, and an acid anhydride group is more preferred.

As described above, the ethylene oxide structure alleviates the positive charge of the nitrogen atom of the quaternary ammonium salt and allows the quaternary ammonium salt to exist stably through electron donation from an unshared electron pair on an oxygen atom. Therefore, the electroconductivity of the resin layer according to the present invention is increased. In addition, the binder resin may be obtained through a reaction with a polyisocyanate compound, an epoxy compound, or the like, which reacts with the hydroxyl group, mercapto group, amino group, and acid anhydride group.

It should be noted that, when the quaternary ammonium salt according to the present invention is fixed in the resin layer, its seeping is suppressed. Therefore, the effects according to the present invention are exhibited particularly in the case of using such resin layer as the surface layer. Such case is preferred also from the viewpoints that the surface layer serves as an ion electroconductive layer and hence the electric resistance on the surface of the charging roller can be uniformly controlled, and overdischarge caused by a local reduction in resistance is suppressed.

The quaternary ammonium salt according to the present invention may be added in an amount required for achieving desired electroconductivity. It is desired to blend the quaternary ammonium salt in an amount of 0.5 part by mass or more and 20 parts by mass or less with respect to 100 parts by mass of the binder resin. When the blended amount is 0.5 part by mass or more, an electroconductivity-providing effect exhibited by the addition of the quaternary ammonium salt can be easily obtained. When the blended amount is 20 parts by mass or less, the movement of the quaternary ammonium salt toward the surface of the binder resin can be more suppressed.

As a guide, the electric resistance of the electroconductive member for electrophotography according to the present invention is $1\times10^3$ Ω·cm or more and $1\times10^9$ Ω·cm or less. However, the case where the electric resistance is set to $1\times10^5$ Ω·cm or more and $1\times10^8$ Ω·cm or less is effective. When the electric resistance is set to $1\times10^5$ Ω·cm or more, the occurrence of abnormal discharge due to a leak can be suppressed, and when the electric resistance is set to $1\times10^8$ Ω·cm or less, the occurrence of an image detrimental effect due to an insufficient electric resistance can be suppressed.

<Electrophotographic Image Forming Apparatus>
[Electrophotographic Apparatus]

Figure 2:
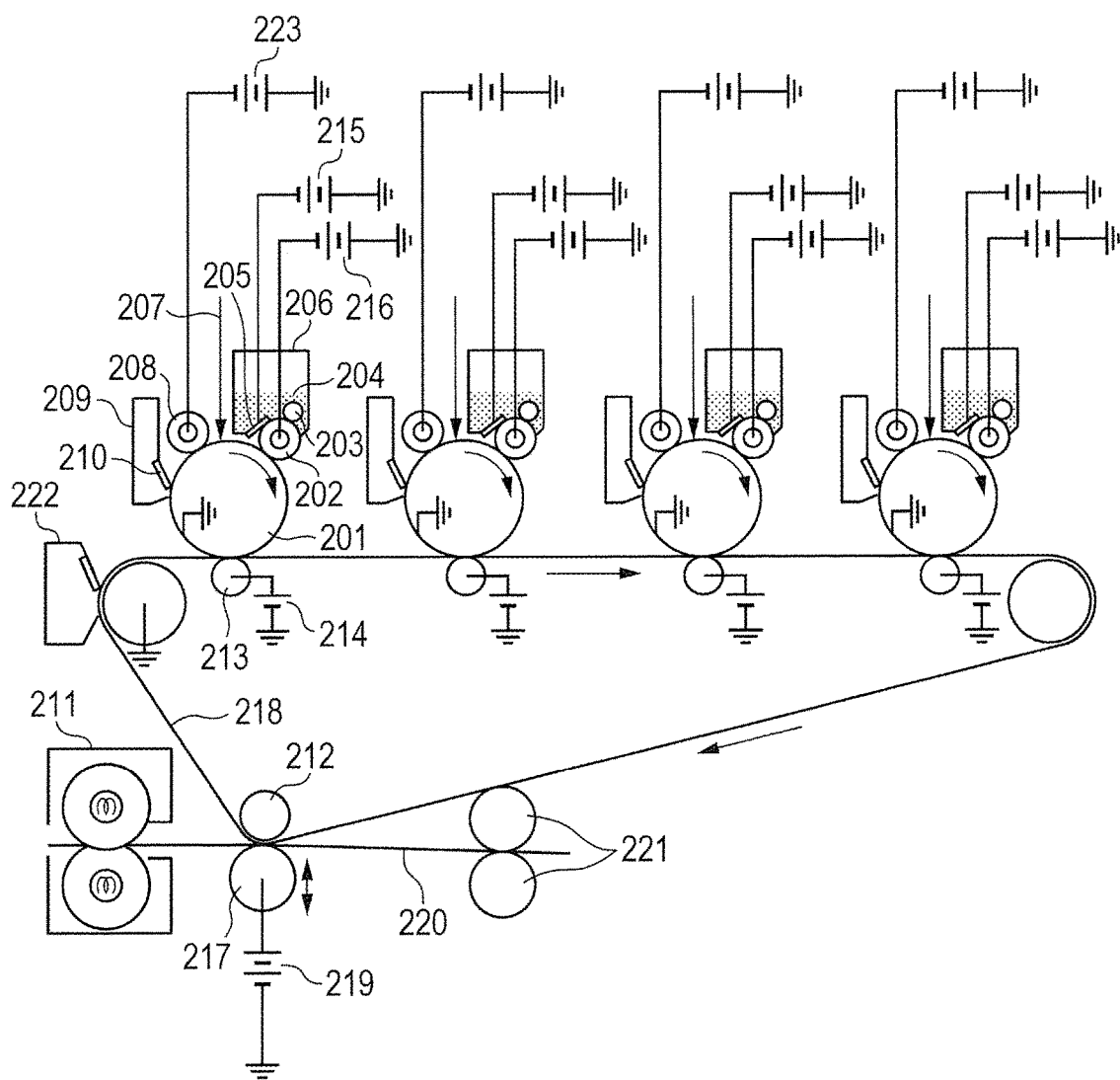
FIG. 2 is a schematic view of an electrophotographic image forming apparatus.
Figure 3:
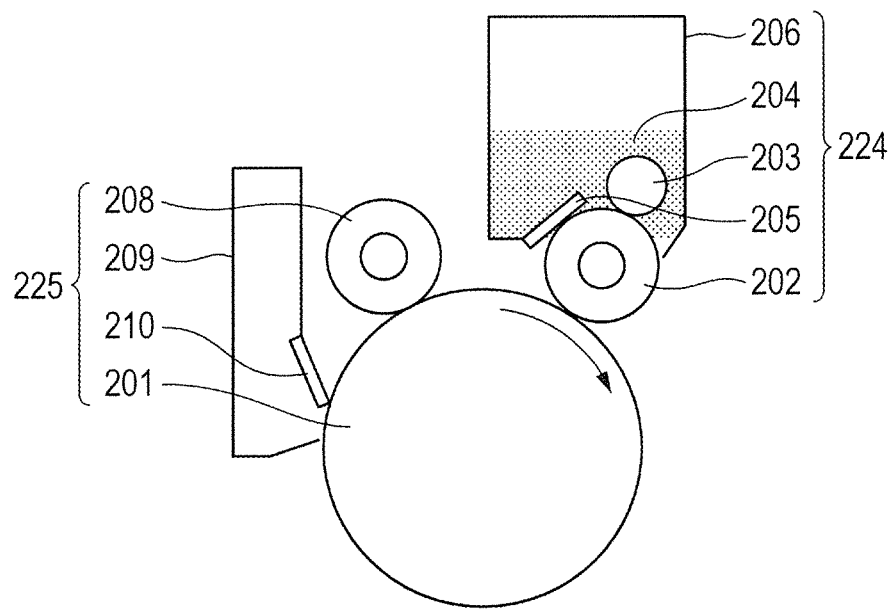
FIG. 3 is a schematic view of a process cartridge.

A schematic configuration view of an electrophotographic image forming apparatus including the electroconductive member for electrophotography according to the present invention is illustrated in FIG. 2. The electrophotographic image forming apparatus is, for example, a color electrophotographic image forming apparatus in which a process cartridge illustrated in FIG. 3 is provided for each color ink, e.g., black, magenta, yellow, and cyan, and the process cartridge is removably mounted thereonto.

The process cartridge is removably mounted onto a main body of the electrophotographic image forming apparatus. The process cartridge includes at least one of a developing device 224 or a charging device 225.

The developing device 224 is obtained by integrating at least a developing roller 202, a toner supplying roller 203, a toner 204, a toner regulating blade 205, and a toner container 206.

The charging device 225 is obtained by integrating at least a photosensitive member 201, a cleaning blade 210, and a charging roller 208. Voltages are applied to the developing roller 202 and the toner regulating blade 205 from a developing bias power source 216 and a blade bias power source 215, respectively.

In the case where the process cartridge according to the present invention includes the developing device 224, at least one of the developing roller 202, the toner supplying roller 203, or the toner regulating blade 205 is formed of the electroconductive member for electrophotography according to the present invention. It is particularly preferred that the developing roller 202 be formed of the electroconductive member for electrophotography according to the present invention. When the developing roller 202 is formed of the electroconductive member for electrophotography according to the present invention, the electric resistance is less liable to change through electrification, and an electrophotographic image of high quality can be formed stably.

In addition, in the case where the process cartridge according to the present invention includes the charging device 225, at least one of the charging roller 208, the cleaning blade 210, or the toner regulating blade 205 is formed of the electroconductive member for electrophotography according to the present invention. It is particularly preferred that the charging roller 208 be formed of the electroconductive member for electrophotography according to the present invention. When the charging roller 208 is formed of the electroconductive member for electrophotography according to the present invention, the electric resistance is less liable to change through electrification, and an electrophotographic image of high quality can be formed stably.

In addition, the photosensitive member 201 rotates in a direction indicated by the arrow and is uniformly charged by the charging roller 208 to which a voltage has been applied from a charging bias power source 223, and an electrostatic latent image is formed on its surface by laser light 207. The toner 204 conveyed by the developing roller 202 arranged so as to be brought into contact with the photosensitive member 201 is applied to the electrostatic latent image to develop the image, and thereby the image is visualized as a toner image. The visualized toner image on the photosensitive member is transferred onto an intermediate transfer belt 218 by a primary transfer roller 213 to which a voltage has been applied by a primary transfer bias power source 214. The toner images of the respective colors are sequentially superimposed to form a color image on the intermediate transfer belt.

Paper 220 is fed into the apparatus by a sheet-feeding roller 221, and is then conveyed into a gap between the intermediate transfer belt 218 backed up by a secondary transfer counter roller 212 and a secondary transfer roller 217. A voltage is applied from a secondary transfer bias power source 219 to the secondary transfer roller 217, and the color image on the intermediate transfer belt is transferred onto the paper 220 by the application of the voltage through the paper 220. The paper 220 onto which the color image has been transferred is subjected to fixing treatment by a fixing device 211, and then discharged to the outside of the apparatus. Thus, a printing operation is completed.

Meanwhile, the toner remaining on the photosensitive member without being transferred is scraped off the surface of the photosensitive member by a cleaning blade 210 and stored in a waste toner-storing container 209. The photosensitive member 201 that has been cleaned repeats the foregoing process. The toner remaining on the primary transfer belt without being transferred is also scraped off by a cleaning apparatus 222.

Examples according to the present invention are described below.

<Production of Quaternary Ammonium Salt>

Quaternary ammonium salts 1 to 24 were synthesized in Synthesis Examples 1 to 24.

Synthesis Example 1

Synthesis of Tertiary Amine 1 as Raw Material 25 g (183 mmol) of p-xylylenediamine as an amine was dissolved in 75 ml of ethanol. Next, while the resultant was cooled in an ice bath, 87.1 g (1.514 mol) of 80% formic acid as a reducing agent and 65.6 g (807 mmol) of a 37% formaldehyde aqueous solution as a tertiarizing agent were added thereto in drops. After the addition in drops, the resultant was heated and refluxed while being stirred for 5 hours. The reaction solution was cooled to room temperature, and ethanol, and excessive formic acid and formaldehyde were distilled away under reduced pressure. 200 ml of a 10% sodium hydroxide aqueous solution was added to the obtained concentrated solution, and then the resultant was subjected to separation three times with 100 ml of ethyl acetate. Magnesium sulfate was added to the obtained organic layer, followed by stirring and then filtration. Ethyl acetate was distilled away under reduced pressure. A tertiary amine 1 as a raw material was synthesized by the operations described above.

Synthesis of Quaternary Ammonium Salt 1

15.6 g (81.12 mmol) of the tertiary amine 1 as a raw material was dissolved in 31 ml of chloroform, and then 30 g (324.5 mmol) of epichlorohydrin was added thereto in drops, and the resultant was stirred at room temperature for 1 day. Next, 200 ml of acetone was added to the obtained liquid to precipitate a crystalline material, and the crystalline material was subjected to filtration. Further, the crystalline material was washed five times with 100 ml of acetone. After that, the crystalline material was recovered and dried under reduced pressure, to yield a quaternary ammonium salt 1.

The obtained quaternary ammonium salt 1 was analyzed with an NMR apparatus (EX-400, manufactured by JEOL Ltd.). Chemical shifts (ppm) using, as a reference, the peak of tetramethylsilane (TMS) in DMSO obtained from a $^1$H-NMR spectrum are shown below.

$^1$H-NMR (400 MHz, DMSO, 22° C.): δ=7.75 (m, 4H), 4.79 (s, 4H), 4.05 (s, 2H), 3.83 (s, 2H), 3.65 (m, 2H), 3.28 (s, 12H, CH$_3$), 3.24 (m, 2H), 2.75 (m, 2H), 2.48 (m, 2H)

As a result of the analysis, it was confirmed that the quaternary ammonium salt 1 had the following structure.

<Quaternary Ammonium Salt 1>

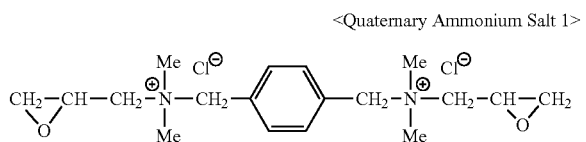

In the formula, Me represents CH$_3$.

Synthesis Examples 2 to 24

Tertiary amines as raw materials were hereinafter synthesized by using amines and tertiarizing agents shown in Table 1 in the same manner as described above, or commercially available ones were purchased. After that, the tertiary amines as raw materials and quaternizing agents were allowed to react with each other, to synthesize target quaternary ammonium salts 2 to 24. In the following formulae, Me represents CH$_3$ and Et represents CH$_2$CH$_3$. It should be noted that, in Synthesis Example without any description of a tertiarizing agent in Table 1, a tertiary amine commercially available as an amine was used.

<Quaternary Ammonium Salt 2>

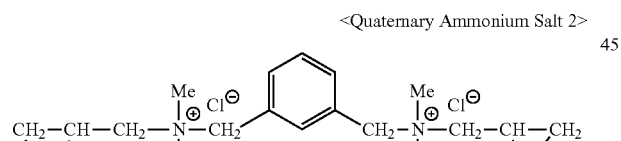

<Quaternary Ammonium Salt 3>

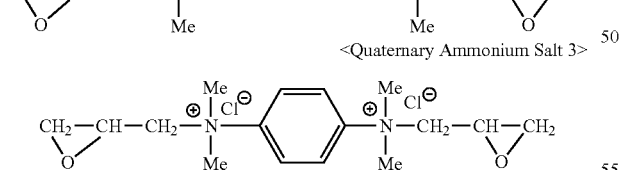

<Quaternary Ammonium Salt 4>

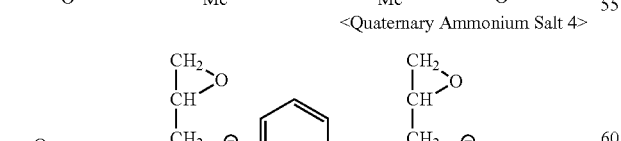

<Quaternary Ammonium Salt 5>

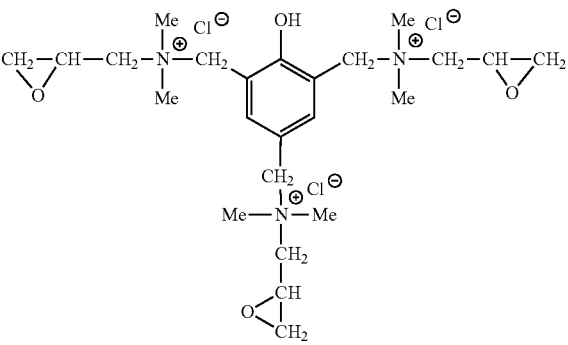

<Quaternary Ammonium Salt 6>

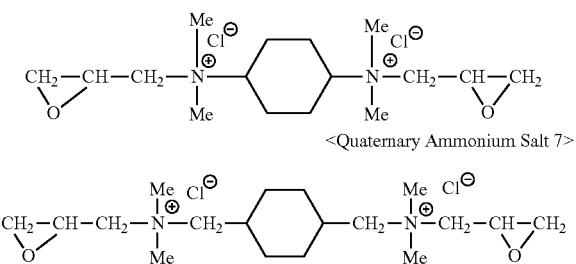

<Quaternary Ammonium Salt 7>

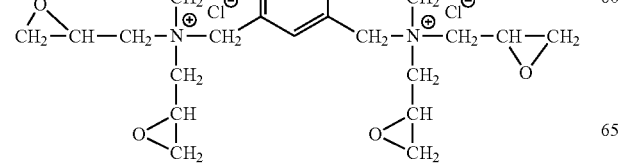

Chemical shifts (ppm) using, as a reference, the peak of TMS in DMSO obtained from a $^1$H-NMR spectrum are shown below.

$^1$H-NMR (400 MHz, DMSO, 22° C.): δ=4.12 (s, 2H), 3.87 (s, 2H), 3.48 (m, 4H), 3.30 (s, 12H, CH$_3$), 3.17 (m, 2H), 2.95 (m, 2H), 2.71 (m, 2H), 2.08-0.98 (8H)

<Quaternary Ammonium Salt 8>

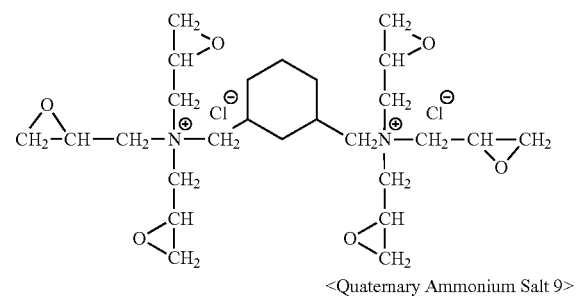

<Quaternary Ammonium Salt 9>

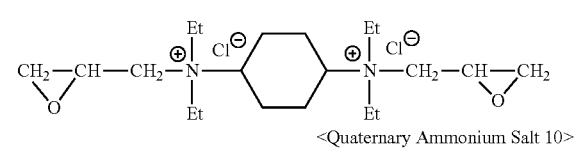

<Quaternary Ammonium Salt 10>

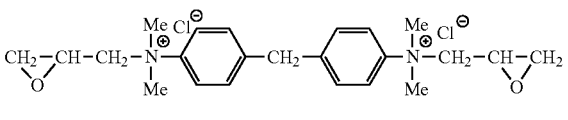

Chemical shifts (ppm) using, as a reference, the peak of TMS in DMSO obtained from a $^1$H-NMR spectrum are shown below.

$^1$H-NMR (400 MHz, DMSO, 22° C.): δ=6.91 (m, 4H), 6.64 (m, 4H), 4.12 (s, 2H), 3.87 (s, 2H), 3.48 (s, 2H), 3.29 (s, 12H, CH$_3$), 3.12 (m, 1H), 2.84 (m, 2H), 2.49 (m, 2H)

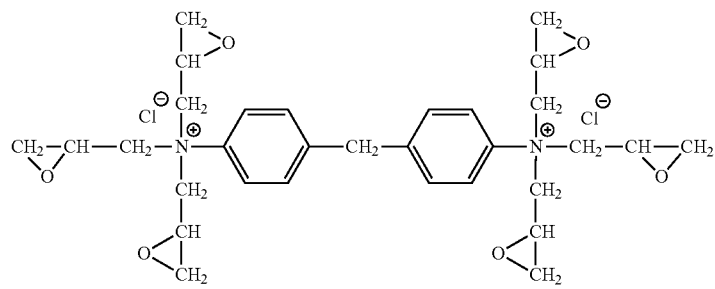

<Quarternary Ammonium Salt 11>

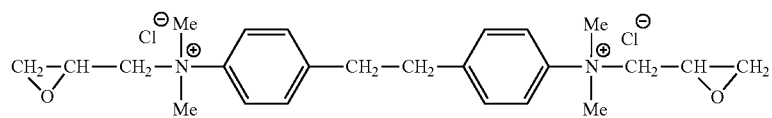

<Quarternary Ammonium Salt 12>

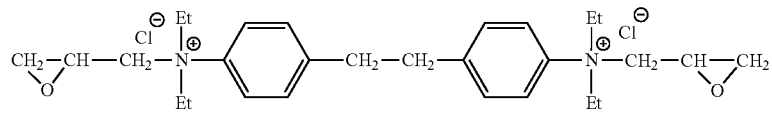

<Quarternary Ammonium Salt 13>

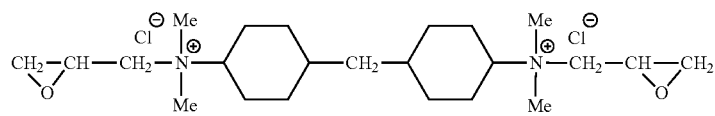

<Quarternary Ammonium Salt 14>

Chemical shifts (ppm) using, as a reference, the peak of TMS in DMSO obtained from a $^1$H-NMR spectrum are shown below.

$^1$H-NMR (400 MHz, DMSO, 22° C.): δ=3.94 (s, 2H), 3.85 (s, 2H), 3.49 (m, 4H), 3.31 (s, 12H, CH$_3$), 3.15 (m, 2H), 2.95 (m, 2H), 2.71 (m, 2H), 1.98-0.84 (8H)

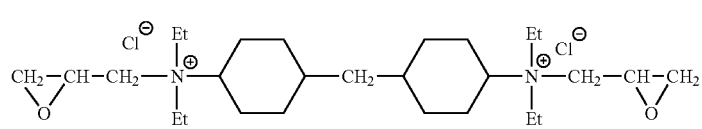

<Quaternary Ammonium Salt 15>

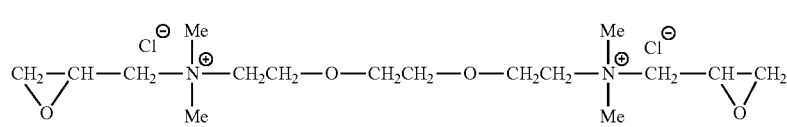

<Quaternary Ammonium Salt 16>

Chemical shifts (ppm) using, as a reference, the peak of TMS in DMSO obtained from a $^1$H-NMR spectrum are shown below.

$^1$H-NMR (400 MHz, DMSO, 22° C.): δ=3.92 (s, 2H), 3.83 (s, 2H), 3.67-3.49 (m, 10H), 3.31 (s, 12H, CH$_3$), 3.25-3.13 (6H), 2.89 (m, 2H), 2.71 (m, 2H)

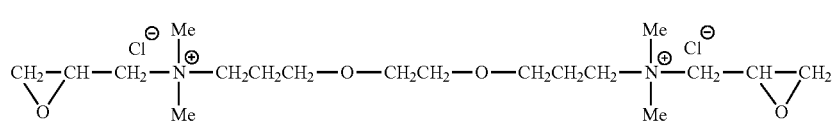

<Quaternary Ammonium Salt 17>

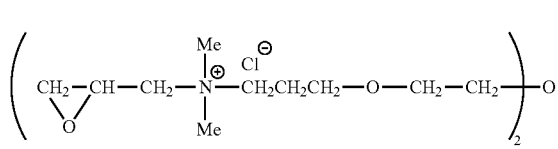

<Quaternary Ammonium Salt 18>

-continued

<Quaternary Ammonium Salt 19>

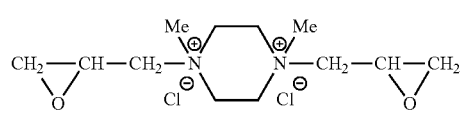

A quaternary ammonium salt 19 was synthesized in the same manner as in the synthesis of the quaternary ammonium salt 1 except that the tertiary amine 1 as a raw material used in the synthesis of the quaternary ammonium salt 1 in Synthesis Example 1 was changed to N,N'-dimethylpiperazine.

<Quaternary Ammonium Salt 20>

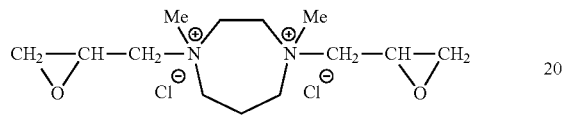

A tertiary amine as a raw material was synthesized in the same manner as in the synthesis of the tertiary amine 1 except that p-xylylenediamine used in the synthesis of the tertiary amine 1 as a raw material in Synthesis Example 1 was changed to homopiperazine. Then, a quaternary ammonium salt 20 was synthesized in the same manner as in the synthesis of the quaternary ammonium salt 1 except that the tertiary amine 1 as a raw material used in the synthesis of the quaternary ammonium salt 1 in Synthesis Example 1 was changed to the tertiary amine synthesized above (N,N'-dimethylhomopiperazine).

<Quaternary Ammonium Salt 21>

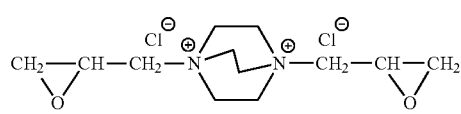

A quaternary ammonium salt 21 was synthesized in the same manner as in the synthesis of the quaternary ammonium salt 1 except that the tertiary amine 1 as a raw material used in the synthesis of the quaternary ammonium salt 1 in Synthesis Example 1 was changed to 1,4-diazabicyclo-2,2,2-octane.

<Quaternary Ammonium Salt 22>

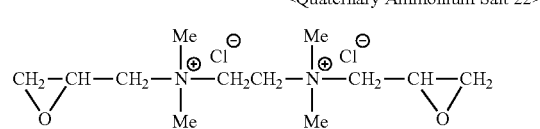

<Quaternary Ammonium Salt 23>

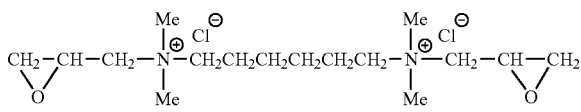

<Quaternary Ammonium Salt 24>

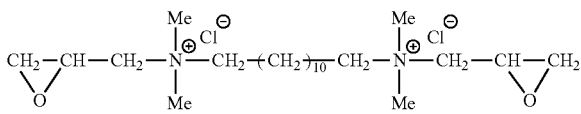

TABLE 1

|  | Quaternary ammonium salt | Tertiary amine as raw material | | |
|---|---|---|---|---|
|  |  | Amine | Tertiarizing agent | Quaternizing agent |
| Formula 1 | 1 | p-Xylylenediamine | Formaldehyde | Epichlorohydrin |
|  | 2 | m-Xylylenediamine | Formaldehyde | Epichlorohydrin |
|  | 3 | N,N,N',N'-Tetramethyl-p-phenylenediamine | — | Epichlorohydrin |
|  | 4 | N,N,N',N'-Tetraglycidyl-m-xylylendiamine | — | Epichlorohydrin |
|  | 5 | 2,4,6,-Tri(dimethylaminomethyl)phenol | — | Epichlorohydrin |
| Formula 2 | 6 | Trans-1,4-cyclohexanediamine | Formaldehyde | Epichlorohydrin |
|  | 7 | 1,4-bis(aminomethyl)cyclohexane | Formaldehyde | Epichlorohydrin |
|  | 8 | N,N,N',N'-Tetraglycidyl-m-cyclohexanediamine | — | Epichlorohydrin |
|  | 9 | Trans-1,4-cyclohexanediamine | Acetaldehyde | Epichlorohydrin |
| Formula 3 | 10 | p-Methylenedianiline | Formaldehyde | Epichlorohydrin |
|  | 11 | N,N,N',N'-Tetraglycidyl-p-methylenebisaniline | — | Epichlorohydrin |
|  | 12 | 4,4'-Ethylenedianiline | Formaldehyde | Epichlorohydrin |
|  | 13 | 4,4'-Ethylenedianiline | Acetaldehyde | Epichlorohydrin |
| Formula 4 | 14 | 4,4'-Methylenebis(cyclohexylamine) | Formaldehyde | Epichlorohydrin |
|  | 15 | 4,4'-Methylenebis(cyclohexylamine) | Acetaldehyde | Epichlorohydrin |
| Formula 5 | 16 | Ethylene glycol bis-3-ethylamine | Formaldehyde | Epichlorohydrin |
|  | 17 | Ethylene glycol bis-3-propylamine | Formaldehyde | Epichlorohydrin |
|  | 18 | Diethylene glycol bispropylamine | Formaldehyde | Epichlorohydrin |
| Formula 6 | 19 | N,N'-Dimethylpiperazine | — | Epichlorohydrin |
|  | 20 | Homopiperazine | Formaldehyde | Epichlorohydrin |
| Formula 7 | 21 | 1,4-Diazabicyclo-2,2,2-octane | — | Epichlorohydrin |

TABLE 1-continued

| | Quaternary ammonium salt | Tertiary amine as raw material | | |
|---|---|---|---|---|
| | | Amine | Tertiarizing agent | Quaternizing agent |
| Formula 8 | 22 | N,N,N',N'-Tetramethyl-ethylenediamine | — | Epichlorohydrin |
| | 23 | N,N,N',N'-Tetramethyl-hexamethylenediamine | — | Epichlorohydrin |
| | 24 | 1,12-Dodecane-diamine | Formaldehyde | Epichlorohydrin |

Example 1

<Production of Test Piece>

| | |
|---|---|
| Epichlorohydrin-ethylene oxide-allyl glycidyl ether terpolymer (GECO) (trade name: EPICHLOMER CG-102, manufactured by Daiso Co., Ltd.) | 100 parts by mass |
| Zinc oxide (Zinc Oxide Type II, manufactured by Seido Chemical Industry Co., Ltd.) | 5 parts by mass |
| Calcium carbonate (trade name: Silver-W, manufactured by Shiraishi Calcium Kaisha, Ltd.) | 35 parts by mass |
| Carbon black (trade name: SEAST SO, manufactured by Tokai Carbon Co., Ltd.) | 0.5 part by mass |
| Stearic acid | 2 parts by mass |
| Adipic acid ester (trade name: POLYCIZER W305ELS, manufactured by Dainippon Ink And Chemicals, Inc.) | 10 parts by mass |
| Quaternary ammonium salt 1 as an ionic electroconductive agent | 2 parts by mass |

The materials whose kinds and amounts were described above were kneaded with a kneader, to prepare an A kneaded rubber composition. Next, 0.5 part by mass of sulfur as a vulcanizing agent and 2 parts by mass of dipentamethylenethiuram tetrasulfide (trade name: Nocceler TRA, manufactured by Ouchi Shinko Chemical Industrial Co., Ltd.) as a vulcanizing aid were added to the A kneaded rubber composition, and the resultant was kneaded with an open roll, to prepare a B kneaded rubber composition.

The prepared B kneaded rubber composition was put in a sheet mold having a thickness of 0.5 mm, and subjected to primary vulcanization for 15 minutes with a hot press heated to 160° C. Next, the rubber sheet taken out from the mold was subjected to secondary vulcanization for 1 hour in an oven at 160° C., to produce a test piece.

<Evaluation of Bleeding of Test Piece>

The test piece was allowed to stand still in an environment of a temperature of 40° C. and a humidity of 95% R.H. for 1 week while being brought into abutment with a polyethylene terephthalate (PET) sheet, and then the surface of the PET sheet was observed with an optical microscope (magnification: 10). The presence or absence of the adhesion of a product bleeding from the test piece was observed, and evaluation was performed based on the following criteria.
A: No bleeding product is observed in the abutting portion.
B: Slight fog is observed in part of the abutting portion.
C: Slight fog is observed in the entire abutting portion.
D: A conspicuous bleeding product is observed in the entire abutting portion.

<Evaluation of Change in Electroconductivity of Test Piece>

Figure 4:
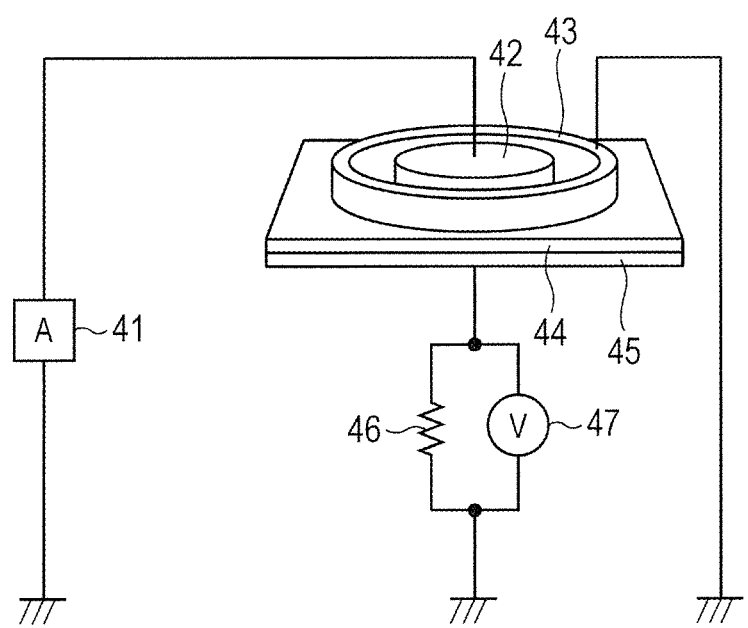
FIG. 4 is a schematic view of an instrument for measuring a current value of a test piece.

A schematic view of an instrument for measuring a current value of the test piece according to the present invention is illustrated in FIG. 4. As illustrated in FIG. 4, a test piece 44 having a thickness of 0.5 mm was brought into abutment with a cylindrical electrode 42 including a plate electrode 45 and a guide link 43, and having a diameter of 1 cm. Next, a direct current of 30 µA was applied from a power source 41 in an environment of a temperature of 23° C. and a humidity of 50% R.H. 2 Seconds after the application of the current, a voltage to be applied to a resistance 46 from the power source 41 was started to be measured with a voltmeter 47, and an initial volume resistance value of the test piece was calculated based on a time average voltage obtained as a result of measurement for 3 seconds. After the measurement of the initial volume resistance value of the test piece, a current of 30 µA was continued to be applied for 5 minutes, and then a volume resistance value of the test piece after electrification was calculated based on a time average voltage obtained as a result of measurement of the voltage to be applied to the resistance 46 from the power source 41 for 3 seconds with the voltmeter 47. A value obtained by dividing the volume resistance value (Ω·cm) of the test piece after 5 minutes calculated as described above by the initial volume resistance value (Ω·cm) of the test piece calculated as described above, (volume resistance value of test piece after 5 minutes/initial volume resistance value of the test piece), was evaluated as a change in electroconductivity through electrification.

Examples 2 to 26

Test pieces were produced and evaluated in the same manner as in Example 1 except that the kinds and added amounts of the quaternary ammonium salts were changed as shown in Table 2-1.

Example 27

<Test Piece>

| | |
|---|---|
| Acrylonitrile-butadiene copolymer (NBR) (trade name: Nipol DN219, manufactured by Zeon Corporation) | 100 parts by mass |
| Zinc oxide (Zinc Oxide Type II, manufactured by Seido Chemical Industry Co., Ltd.) | 5 parts by mass |
| Calcium carbonate (trade name: Silver-W, manufactured by Shiraishi Calcium Kaisha, Ltd.) | 20 parts by mass |
| Carbon black (trade name: SEAST SO, manufactured by Tokai Carbon Co., Ltd.) | 0.5 part by mass |
| Stearic acid | 2 parts by mass |
| Quaternary ammonium salt 10 as an ionic electroconductive agent | 2 parts by mass |

The materials whose kinds and amounts were described above were kneaded with a kneader, to prepare an A kneaded rubber composition. Next, 0.5 part by mass of sulfur as a vulcanizing agent and 2 parts by mass of dipentamethylenethiuram tetrasulfide (trade name: Nocceler TRA, manufactured by Ouchi Shinko Chemical Industrial Co., Ltd.) as a vulcanizing aid were added to the A kneaded rubber composition, and the resultant was kneaded with an open roll, to prepare a B kneaded rubber composition.

The prepared B kneaded rubber composition was put in a sheet mold having a thickness of 0.5 mm, and vulcanized for 15 minutes with a hot press heated to 160° C., to produce a test piece. The test piece was evaluated in the same manner as in Example 1.

Example 28

A test piece was produced and evaluated in the same manner as in Example 27 except that the quaternary ammonium salt 10 was changed to a quaternary ammonium salt shown in Table 2-1.

Example 29

| | |
|---|---|
| Polyethylene glycol glycidyl ether (manufactured by Sigma-Aldrich) | 65 parts by mass |
| Ethylene glycol bis-3-ethylamine (manufactured by Sigma-Aldrich) | 35 parts by mass |
| Quaternary ammonium salt 10 as an ionic electroconductive agent | 2 parts by mass |

The materials whose kinds and amounts were described above were mixed. The mixture was put in a sheet mold having a thickness of 0.5 mm, and heated for 1 hour with a hot press heated to 90° C. and further heated for 1 hour at 160° C., to produce a test piece. The test piece was evaluated in the same manner as in Example 1.

Example 30

A test piece was produced and evaluated in the same manner as in Example 29 except that the quaternary ammonium salt 10 was changed to a quaternary ammonium salt shown in Table 2-1.

Comparative Example 1

A test piece was produced and evaluated in the same manner as in Example 1 except that the ionic electroconductive agent was changed to trimethylhexylammonium chloride.

Comparative Example 2

A test piece was produced and evaluated in the same manner as in Example 27 except that the ionic electroconductive agent was changed to trimethylhexylammonium chloride.

Comparative Example 3

A test piece was produced and evaluated in the same manner as in Example 29 except that the ionic electroconductive agent was changed to trimethylhexylammonium chloride.

The evaluation results of Examples 1 to 30 are shown in Table 2-1, and the evaluation results of Comparative Examples 1 to 3 are shown in Table 2-2.

TABLE 2-1

| Example | Number of quaternary ammonium salt as ionic electroconductive agent | Added amount (part(s) by mass) | EO content (mass %) | Evaluation of bleeding | Initial volume resistivity ($\Omega \cdot cm$) | Volume resistivity after 5 minutes ($\Omega \cdot cm$) | Evaluation of change in electroconductivity |
|---|---|---|---|---|---|---|---|
| 1 | 1 | 2 | 37.2 | B | 3.0E+07 | 3.7E+07 | 1.23 |
| 2 | 2 | 2 | 37.2 | B | 3.5E+07 | 4.5E+07 | 1.29 |
| 3 | 3 | 2 | 37.2 | B | 2.7E+07 | 3.6E+07 | 1.33 |
| 4 | 4 | 2 | 37.2 | B | 3.2E+07 | 3.9E+07 | 1.22 |
| 5 | 5 | 2 | 37.2 | B | 2.5E+07 | 3.0E+07 | 1.20 |
| 6 | 6 | 2 | 37.2 | B | 3.6E+07 | 4.4E+07 | 1.22 |
| 7 | 7 | 2 | 37.2 | B | 3.8E+07 | 4.6E+07 | 1.21 |
| 8 | 8 | 2 | 37.2 | B | 4.2E+07 | 5.2E+07 | 1.24 |
| 9 | 9 | 2 | 37.2 | B | 3.6E+07 | 4.5E+07 | 1.25 |
| 10 | 10 | 2 | 37.2 | B | 6.1E+07 | 6.9E+07 | 1.13 |
| 11 | 11 | 2 | 37.2 | B | 7.1E+07 | 8.2E+07 | 1.15 |
| 12 | 12 | 2 | 37.2 | B | 6.3E+07 | 7.3E+07 | 1.16 |
| 13 | 13 | 2 | 37.2 | B | 7.5E+07 | 8.6E+07 | 1.15 |
| 14 | 14 | 2 | 37.2 | B | 5.6E+07 | 6.7E+07 | 1.20 |
| 15 | 15 | 2 | 37.2 | B | 5.9E+07 | 7.0E+07 | 1.19 |
| 16 | 16 | 2 | 37.2 | B | 1.2E+07 | 1.3E+07 | 1.10 |
| 17 | 17 | 2 | 37.2 | B | 1.8E+07 | 2.0E+07 | 1.11 |
| 18 | 18 | 2 | 37.2 | B | 9.0E+06 | 1.0E+07 | 1.11 |
| 19 | 19 | 2 | 37.2 | B | 3.5E+07 | 4.2E+07 | 1.20 |
| 20 | 20 | 2 | 37.2 | B | 3.8E+07 | 4.8E+07 | 1.26 |
| 21 | 21 | 2 | 37.2 | B | 3.5E+07 | 4.2E+07 | 1.20 |
| 22 | 22 | 2 | 37.2 | B | 2.3E+07 | 3.0E+07 | 1.30 |
| 23 | 23 | 2 | 37.2 | B | 3.5E+07 | 4.3E+07 | 1.23 |
| 24 | 24 | 2 | 37.2 | B | 3.7E+07 | 4.5E+07 | 1.22 |
| 25 | 16 | 0.5 | 37.2 | B | 5.6E+07 | 6.5E+07 | 1.16 |
| 26 | 16 | 20 | 37.2 | C | 6.5E+06 | 7.0E+07 | 1.08 |
| 27 | 10 | 2 | 0 | B | 8.5E+07 | 9.9E+07 | 1.16 |
| 28 | 16 | 2 | 0 | B | 6.5E+07 | 7.2E+07 | 1.11 |
| 29 | 10 | 2 | 71.8 | A | 7.5E+06 | 8.0E+06 | 1.07 |
| 30 | 16 | 2 | 71.8 | A | 5.3E+06 | 5.6E+06 | 1.06 |

TABLE 2-2

| Comparative Example | Number of quaternary ammonium salt as ionic electroconductive agent | Added amount (part(s) by mass) | EO content (mass %) | Evaluation of bleeding | Initial volume resistivity (Ω · cm) | Volume resistivity after electrification (Ω · cm) | Evaluation of change in electroconductivity |
|---|---|---|---|---|---|---|---|
| 1 | — | 2 | 37.2 | C | 3.5E+07 | 5.5E+07 | 1.57 |
| 2 | — | 2 | 0 | D | 9.1E+07 | 1.60E+08 | 1.76 |
| 3 | — | 2 | 71.8 | C | 6.5E+06 | 1.0E+07 | 1.54 |

In Tables 2-1 and 2-2, the "E+o" as the values of the initial volume resistivity and the volume resistivity after electrification represents 10 to the power of the "o".

Example 31

<Production of Electroconductive Elastic Roller>

| | |
|---|---|
| Epichlorohydrin-ethylene oxide-allyl glycidyl ether terpolymer (GECO) (trade name: EPICHLOMER CG-102, manufactured by Daiso Co., Ltd.) | 100 parts by mass |
| Zinc oxide (Zinc Oxide Type II, manufactured by Seido Chemical Industry Co., Ltd.) | 5 parts by mass |
| Calcium carbonate (trade name: Silver-W, manufactured by Shiraishi Calcium Kaisha, Ltd.) | 35 parts by mass |
| Carbon black (trade name: SEAST SO, manufactured by Tokai Carbon Co., Ltd.) | 0.5 part by mass |
| Stearic acid | 2 parts by mass |
| Adipic acid ester (trade name: POLYCIZER W305ELS, manufactured by Dainippon Ink And Chemicals, Inc.) | 10 parts by mass |
| Quaternary ammonium salt 1 as an ionic electroconductive agent | 2 parts by mass |

The materials whose kinds and amounts were described above were kneaded with a kneader, to prepare an A kneaded rubber composition. Next, 0.5 part by mass of sulfur as a vulcanizing agent and 2 parts by mass of dipentamethylenethiuram tetrasulfide (trade name: Nocceler TRA, manufactured by Ouchi Shinko Chemical Industrial Co., Ltd.) as a vulcanizing aid were added to the A kneaded rubber composition, and the resultant was kneaded with an open roll, to prepare a B kneaded rubber composition.

Next, a crosshead extruder having a mechanism for supplying an electroconductive shaft core and a mechanism for discharging an electroconductive roller was prepared. The speed at which the metal core was conveyed was adjusted to 60 mm/sec, a die having an inner diameter of 12.5 mmφ was attached to a crosshead, and the temperatures of the extruder and the crosshead were adjusted to 80° C. A layer of an unvulcanized rubber composition was formed around the electroconductive shaft core supplied to the crosshead, the shaft core being formed of a stainless-steel bar having an outer diameter of 6 mmφ and a length of 258 mm. Next, the electroconductive shaft core whose peripheral surface was coated with the layer of the B kneaded rubber composition was loaded into a hot-air vulcanization furnace at 170° C. and heated for 60 minutes, to cross-link the layer of the B kneaded rubber composition. Thus, a rubber elastic layer was formed. After that, end portions were cut and removed so that the rubber elastic layer had a length of 228 mm. Finally, the surface of the rubber elastic layer was ground with sharpening wheels. Thus, an electroconductive elastic roller according to the present invention having such a crown shape that a diameter at the central portion was 12 mm and an average diameter at positions distant from the central portion toward both end portions by 90 mm each was 11.8 mm was obtained.

<Production of Surface Layer>

A surface layer was formed on the electroconductive elastic roller in accordance with the following method. Methyl isobutyl ketone was added to a caprolactone-modified acrylic polyol solution and then the solid content was adjusted to 10 mass %. A mixed solution was prepared by placing 15 parts by mass of carbon black (HAF), 35 parts by mass of needle-like rutile-type titanium oxide fine particles, 0.1 part by mass of modified dimethyl silicone oil, and 80.14 parts by mass of a mixture containing butanone oxime block bodies of hexamethylene diisocyanate (HDI) and isophorone diisocyanate (IPDI) at 7:3 in 100 parts by mass of the acrylic polyol solution in terms of solid content. At this time, the mixture of the block HDI and the block IPDI was added so that the ratio of "NCO/OH=1.0" was satisfied.

210 g of the mixed solution and 200 g of glass beads having an average particle diameter of 0.8 mm as media were mixed in a 450 ml glass bottle, and were then dispersed with a paint shaker dispersing machine for 24 hours. After the dispersion, 5.44 parts by mass (amount corresponding to 20 parts by weight with respect to 100 parts by weight of the acrylic polyol) of cross-linking type acrylic particles (trade name: MR50G; manufactured by Soken Chemical & Engineering Co., Ltd.) as resin particles were added to the resultant, followed by dispersion for an additional 30 minutes. Thus, a paint for forming a surface layer was obtained.

The outer periphery of the electroconductive elastic roller obtained in the foregoing was subjected to dip coating once with the resultant paint for forming a surface layer. The resultant coated product was air-dried at normal temperature for 30 minutes or more. Next, the product was dried in a hot air-circulating dryer set to 90° C. for 1 hour. Further, the product was dried in a hot air-circulating dryer set to 160° C. for 1 hour. Thus, the surface layer was formed on the electroconductive elastic roller. The immersion time of the dip coating was set to 9 seconds, the initial lifting speed of the dip coating was set to 20 mm/sec, and the final lifting speed of the dip coating was set to 2 mm/sec. The lifting speed was linearly changed with time from 20 mm/sec to 2 mm/sec. Thus, a charging roller including the surface layer was produced.

Next, the obtained charging roller was subjected to the following evaluation tests.

<Evaluation of Change in Roller Resistance Value>

Figure 5A:
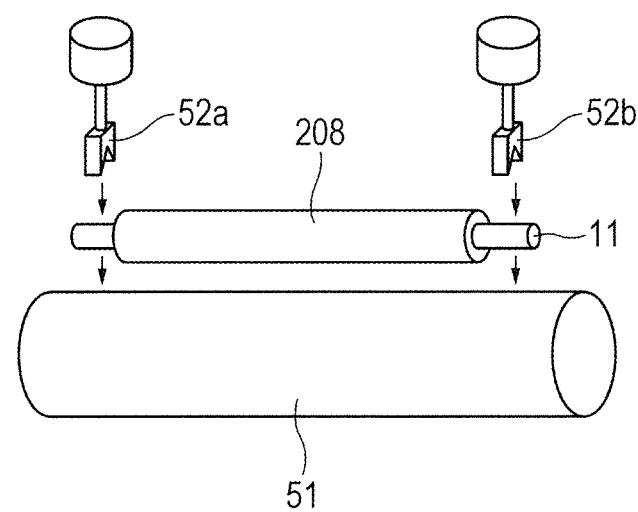
FIG. 5A is a schematic view of an instrument for measuring a current value of the charging roller, in a state prior to measurement.
Figure 5B:
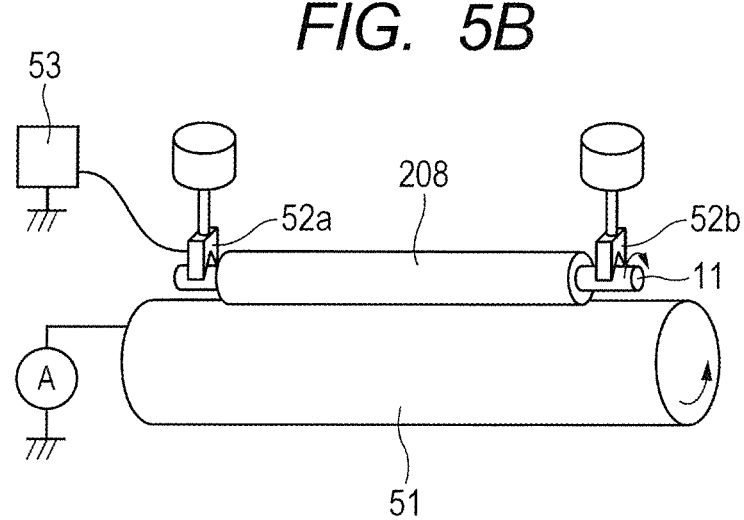
FIG. 5B is a schematic view of the instrument for measuring a current value of the charging roller, at the time of measurement.

A schematic view of an instrument for measuring a current value of the charging roller according to the present invention is illustrated in each of FIG. 5A and FIG. 5B. As illustrated in FIG. 5A and FIG. 5B, the current value of the charging roller according to the present invention is measured when the charging roller is electrified while being brought into abutment with a cylindrical metal (not shown)

having a circle cross section, which has the same curvature as that of a photosensitive member, with the same load as that in the use state of the roller when used in an image forming apparatus of an electrophotographic type (hereinafter also referred to as "electrophotographic image forming apparatus") applied to the roller. In FIG. 5A, bearings 52a and 52b fixed to weights apply pressing stresses downward in the vertical direction to both ends of the electroconductive shaft core 11 of the charging roller 208. A cylindrical metal 51 is positioned in parallel to the charging roller 208 in a downward direction vertical to the charging roller 208. Then, while the cylindrical metal 51 is rotated by a drive device (not shown), the charging roller 208 is pressed against the bearings 52a and 52b as illustrated in FIG. 5B. A direct current of 450 µA is applied by a power source 53, while the cylindrical metal 51 is rotated at a rotary speed similar to that of the photosensitive member in the use state and the charging roller 208 is driven to rotate. 2 Seconds after the application of the current, a time average voltage to be applied from the power source (not shown) was started to be measured with a voltmeter A, and an initial roller resistance value of the charging roller was calculated based on a time average voltage obtained as a result of measurement for 5 seconds. After the measurement of the initial roller resistance value of the roller, a current of 450 µA was continued to be applied for 10 minutes, and then a time average voltage to be applied from the power source 53 was started to be measured with the voltmeter A, and a roller resistance value of the charging roller after electrification was calculated based on a time average voltage obtained as a result of measurement for 5 seconds. Then, a value obtained by dividing the roller resistance value of the roller 10 minutes after the application of the current by the initial roller resistance value of the roller, (roller resistance value of the roller after 10 minutes/initial roller resistance value of the roller), was evaluated as a change in electroconductivity through electrification. In Example 31, the charging roller was left to stand for 48 hours in an environment of a temperature of 23° C. and a humidity of 50% R.H. (N/N environment). After that, in respective environments, loads of 5 N were applied to both the ends of the shaft core to bring the charging roller into abutment with the cylindrical metal having a diameter of 30 mm, and a change in roller resistance value of the roller was determined while the cylindrical metal was rotated at a peripheral speed of 150 mm/s.

<Evaluation of Continuous Image Output Endurance>

Density unevenness like fine streaks (horizontal streak) may occur in a half-tone image with changes in electroconductivity of the charging roller through electrification (increase in electric resistance). Such image is referred to as "horizontal streak image". The horizontal streak image tends to be more deteriorated with a larger change in electroconductivity, and tends to be conspicuous along with long-term utilization. In view of the foregoing, the following evaluation was performed.

The charging roller obtained as described above was mounted as a charging roller onto a laser printer of an electrophotographic type (trade name: Laserjet 4515n, manufactured by Hewlett-Packard Company). It should be noted that the laser printer had an output speed of a recording medium of 370 mm/sec and an image resolution of 1,200 dpi, and a DC applied voltage of −600 V and an AC applied voltage of Vpp=1,200 V having a frequency of 2,931 Hz were applied to the charging roller. Then, an endurance test in which an image having a print density of 4% (image in which horizontal lines each having a width of 2 dots were drawn in a direction perpendicular to the rotation direction of the photosensitive member at an interval of 50 dots) was continuously output at a process speed of 370 mm/sec was performed. In addition, at an initial stage, and after output of the image on 10,000 sheets, 20,000 sheets, and 32,000 sheets, a half-tone image (image in which horizontal lines each having a width of 1 dot were drawn in a direction perpendicular to the rotation direction of the photosensitive member at an interval of 2 dots) was output in order to check the image. The obtained image was visually observed, and evaluated for density unevenness like fine streaks (horizontal streak).

A: A level at which no horizontal streak arises.

B: A level at which a slight horizontal streak arises only in edge portions of the image.

C: A level at which a slight horizontal streak arises in edge portions and a central portion of the image, but causes no practical problem.

D: A level at which a conspicuous horizontal streak arises in an approximately half region of the image.

Examples 32 to 58

Charging rollers were produced and evaluated in the same manner as in Example 31 except that the kinds and added amounts of the quaternary ammonium salts were changed as shown in Tables 5-1 to 5-2.

Example 59

| | |
|---|---|
| Acrylonitrile-butadiene copolymer (NBR) (trade name: Nipol DN219, manufactured by Zeon Corporation) | 100 parts by mass |
| Zinc oxide (Zinc Ozide Type II, manufactured by Seido Chemical Industry Co., Ltd.) | 5 parts by mass |
| Calcium carbonate (trade name: Silver-W, manufactured by Shiraishi Calcium Kaisha, Ltd.) | 20 parts by mass |
| Carbon black (trade name: SEAST SO, manufactured by Tokai Carbon Co., Ltd.) | 0.5 part by mass |
| Stearic acid | 2 parts by mass |
| Quaternary ammonium salt 10 as an ionic electroconductive agent | 2 parts by mass |

The materials whose kinds and amounts were described above were kneaded with a kneader, to prepare an A kneaded rubber composition. Next, 0.5 part by mass of sulfur as a vulcanizing agent and 2 parts by mass of dipentamethylenethiuram tetrasulfide (trade name: Nocceler TRA, manufactured by Ouchi Shinko Chemical Industrial Co., Ltd.) as a vulcanizing aid were added to the A kneaded rubber composition, and the resultant was kneaded with an open roll, to prepare a B kneaded rubber composition.

A charging roller was produced and evaluated in the same method as in Example 31 except the foregoing.

Example 60

A charging roller was produced and evaluated in the same manner as in Example 59 except that the quaternary ammonium salt 10 was changed to a quaternary ammonium salt shown in Table 5-2.

Example 61

| | |
|---|---|
| Polyethylene glycol glycidyl ether (manufactured by Sigma-Aldrich) | 65 parts by mass |
| Ethylene glycol bis-3-ethylamine (manufactured by Sigma-Aldrich) | 35 parts by mass |
| Quaternary ammonium salt 10 as an ionic electroconductive agent | 2 parts by mass |

The materials whose kinds and amounts were described above were mixed to prepare a raw material for a binder resin. Next, an electroconductive shaft core formed of a stainless steel bar having an outer diameter of 6 mmϕ and a length of 258 mm was arranged in a mold, and the raw material for a binder resin was injected into a cavity formed in the mold. After that, the mold into which the raw material for a binder resin had been injected was heated at 90° C. for 1 hour, and further heated at 160° C. for 1 hour. Then, the resultant was released from the mold after the mold had been cooled to room temperature. Thus, an elastic layer having a thickness of 3.0 mm was formed on the outer periphery of the electroconductive shaft core. A charging roller thus produced was evaluated in the same manner as in Example 31.

Example 62

A charging roller was produced and evaluated in the same manner as in Example 61 except that the quaternary ammonium salt 10 was changed to a quaternary ammonium salt shown in Table 5-2.

Example 63

<Production of Electroconductive Elastic Roller>

An electroconductive elastic roller was produced in the same manner as in Example 31 except that the quaternary ammonium salt 1 was changed to a quaternary ammonium salt (trade name: ADK CIZER LV-70, manufactured by ADEKA Corporation).

<Production of Surface Layer>

0.47 g of the quaternary ammonium salt 1 as an ionic electroconductive agent, and 10.08 g (15.75 mmol) of polypropylene glycol diglycidyl ether (weight average molecular weight: 640), 7.2 g (18.95 mmol) of polypropylene glycol diglycidyl ether (weight average molecular weight: 380), and 6.72 g (16.8 mmol) of polypropylene glycol bis(2-aminopropyl ether) (weight average molecular weight: 400) as binder resins as raw materials were dissolved in isopropyl alcohol (IPA), and the resultant was adjusted so as to achieve a solid content of 27 wt %, to yield a paint for forming a surface layer. The obtained paint for forming a surface layer was applied once onto the outer periphery of the electroconductive elastic roller by dip coating, and air-dried at normal temperature for 30 minutes, followed by drying in a hot air-circulating dryer set to 90° C. for 1 hour and further in a hot air-circulating dryer set to 160° C. for 1 hour. Thus, a surface layer was formed on the elastic layer. It should be noted that the immersion time of the dip coating was set to 9 seconds, the initial lifting speed of the dip coating was set to 20 mm/sec, and the final lifting speed of the dip coating was set to 2 mm/sec. The lifting speed was linearly changed with time from 20 mm/sec to 2 mm/sec.

A charging roller thus produced was evaluated in the same manner as in Example 31.

Examples 64 to 74

Charging rollers were produced and evaluated in the same manner as in Example 63 except that paints for forming surface layers were prepared by using materials shown in Table 3 and surface layers having compositions shown in Table 4 were formed.

Example 75

<Production of Electroconductive Elastic Roller>

An electroconductive elastic roller was produced in the same manner as in Example 59 except that the quaternary ammonium salt 10 was changed to 30 parts by mass of carbon black (trade name: TOKABLACK #7360SB, manufactured by Tokai Carbon Co., Ltd.).

<Production of Surface Layer>

A charging roller was produced and evaluated in the same manner as in Example 63 except that a paint for forming a surface layer was prepared by using materials shown in Table 3 and a surface layer having a composition shown in Table 4 was formed.

Examples 76 to 86

<Production of Electroconductive Elastic Roller>

Electroconductive elastic rollers were produced in the same manner as in Example 63.

<Production of Surface Layer>

Charging rollers were produced and evaluated in the same manner as in Example 63 except that paints for forming surface layers were prepared by using materials shown in Table 3 and surface layers having compositions shown in Table 4 were formed.

Example 87

<Production of Electroconductive Elastic Roller>

An electroconductive elastic roller was produced in the same manner as in Example 63.

<Production of Intermediate Layer>

An intermediate layer was produced in the same manner as with the surface layer in Example 63.

<Production of Surface Layer>

A surface layer was produced in the same manner as with the surface layer in Example 31. Thus, a charging roller was produced. The produced charging roller was evaluated in the same manner as in Example 31.

TABLE 3

| | Raw material for surface layer |
|---|---|
| A | Polyethylene glycol diglycidyl ether |
| B | Polypropylene glycol diglycidyl ether |
| C | Polypropylene glycol bis(2-aminopropyl ether) |
| D | Resol-type phenol resin solution (containing 50 wt % of methanol) |
| E | Hexamethylene diisocyanate |
| F | Hexanediol |
| G | Polyethylene glycol |
| H | n-Butyl acrylate |
| I | Methyl methacrylate |
| J | Polyethylene glycol diacrylate |
| K | 4-Methylhexahydrophthalic anhydride |
| L | 1,2-Ethanedithiol |
| M | 3,6-Dioxa-1,8-ocatanedithiol |
| N | Ethylene glycol bis-3-ethylamine |
| O | Ethylene-vinyl alcohol copolymer |
| P | N-Methoxymethylated nylon |

TABLE 4

| Example | Number of quaternary ammonium salt as ionic electroconductive agent | Added amount (part(s) by mass) | Raw material for surface layer | Added amount (part(s) by mass) | EO content (mass %) |
|---|---|---|---|---|---|
| 63 | 1 | 2 | A/B/C | 42/30/28 | 48.2 |
| 64 | 6 | 2 | A/B/C | 42/30/28 | 48.2 |
| 65 | 10 | 2 | A/B/C | 42/30/28 | 48.2 |
| 66 | 14 | 2 | A/B/C | 42/30/23 | 48.2 |
| 67 | 16 | 2 | A/B/C | 42/30/28 | 48.2 |
| 68 | 19 | 2 | A/B/C | 42/30/28 | 48.2 |
| 69 | 21 | 2 | A/B/C | 42/30/28 | 48.2 |
| 70 | 22 | 2 | A/B/C | 42/30/28 | 48.2 |
| 71 | 16 | 0.5 | A/B/C | 42/30/28 | 48.2 |
| 72 | 16 | 20 | A/B/C | 42/30/28 | 48.2 |
| 73 | 16 | 2 | B/C | 57/43 | 0 |
| 74 | 16 | 2 | A/N | 57/43 | 71.8 |
| 75 | 16 | 2 | A/B/C | 42/30/28 | 48.2 |
| 76 | 16 | 2 | E/F | 61/39 | 0 |
| 77 | 16 | 2 | E/G | 49/51 | 46.7 |
| 78 | 10 | 2 | A/D | 65/35 | 50 |
| 79 | 16 | 2 | A/D | 65/35 | 50 |
| 80 | 10 | 2 | H/I | 59/41 | 0 |
| 81 | 10 | 2 | I/J | 19/81 | 47.2 |
| 82 | 16 | 2 | A/K | 65/35 | 50 |
| 83 | 16 | 2 | A/L | 65/35 | 50 |
| 84 | 16 | 2 | A/M | 65/35 | 71.8 |
| 85 | 16 | 2 | 0 | 100 | 0 |
| 86 | 16 | 2 | P | 100 | 0 |

Comparative Example 4

A charging roller was produced and evaluated in the same manner as in Example 31 except that the ionic electroconductive agent was changed to trimethylhexylammonium chloride.

Comparative Example 5

A charging roller was produced and evaluated in the same manner as in Example 61 except that the ionic electroconductive agent was changed to trimethylhexylammonium chloride.

Comparative Example 6

A charging roller was produced and evaluated in the same manner as in Example 63 except that the ionic electroconductive agent for the surface layer was changed to trimethylhexylammonium chloride.

Comparative Example 7

A charging roller was produced and evaluated in the same manner as in Example 87 except that the ionic electroconductive agent for the intermediate layer was changed to trimethylhexylammonium chloride.

The evaluation results of Examples 31 to 87 are shown in Tables 5-1 and 5-2. In addition, the evaluation results of Comparative Examples 4 to 7 are shown in Table 5-3.

TABLE 5-1

| Example | Quaternary ammonium salt as ionic electroconductive agent | Added amount (part(s) by mass) | Evaluation of image | Initial resistivity of roller | Resistivity of roller after 10 minutes | Evaluation of change in electroconductivity |
|---|---|---|---|---|---|---|
| 31 | 1 | 2 | A | 1.1E+07 | 1.3E+07 | 1.18 |
| 32 | 2 | 2 | B | 1.4E+07 | 1.7E+07 | 1.21 |
| 33 | 3 | 2 | B | 9.8E+06 | 1.2E+07 | 1.22 |
| 34 | 4 | 2 | B | 1.7E+07 | 2.1E+07 | 1.24 |
| 35 | 5 | 2 | B | 8.2E+06 | 1.0E+07 | 1.22 |
| 36 | 6 | 2 | A | 1.5E+07 | 1.8E+07 | 1.20 |
| 37 | 7 | 2 | B | 1.6E+07 | 2.0E+07 | 1.25 |
| 38 | 8 | 2 | A | 2.0E+07 | 2.4E+07 | 1.20 |
| 39 | 9 | 2 | A | 2.1E+07 | 2.5E+07 | 1.19 |
| 40 | 10 | 2 | A | 3.2E+07 | 3.5E+07 | 1.09 |
| 41 | 11 | 2 | A | 3.6E+07 | 4.0E+07 | 1.11 |
| 42 | 12 | 2 | A | 3.3E+07 | 3.6E+07 | 1.09 |
| 43 | 13 | 2 | A | 3.8E+07 | 4.2E+07 | 1.11 |
| 44 | 14 | 2 | A | 3.7E+07 | 4.2E+07 | 1.14 |
| 45 | 15 | 2 | A | 4.0E+07 | 4.5E+07 | 1.13 |
| 46 | 16 | 2 | A | 6.0E+06 | 6.5E+06 | 1.08 |
| 47 | 17 | 2 | A | 6.5E+06 | 7.0E+06 | 1.08 |
| 48 | 18 | 2 | A | 6.3E+06 | 6.8E+06 | 1.08 |
| 49 | 19 | 2 | B | 1.1E+07 | 1.4E+07 | 1.27 |
| 50 | 20 | 2 | B | 1.3E+07 | 1.6E+07 | 1.23 |
| 51 | 21 | 2 | B | 1.5E+07 | 1.9E+07 | 1.27 |
| 52 | 22 | 2 | B | 8.7E+06 | 1.1E+07 | 1.26 |
| 53 | 23 | 2 | B | 1.5E+07 | 1.9E+07 | 1.27 |
| 54 | 24 | 2 | B | 2.1E+07 | 2.6E+07 | 1.24 |

TABLE 5-2

| Example | Quaternary ammonium salt as ionic electroconductive agent | Added amount (part(s) by mass) | Evaluation of image | Initial resistivity of roller | Resistivity of roller after 10 minutes | Evaluation of change in electroconductivity |
|---|---|---|---|---|---|---|
| 55 | 16 | 0.5 | A | 1.0E+07 | 1.1E+07 | 1.10 |
| 56 | 16 | 5 | A | 5.0E+06 | 5.2E+06 | 1.04 |
| 57 | 16 | 10 | A | 4.3E+06 | 4.4E+06 | 1.02 |
| 58 | 16 | 20 | A | 3.9E+06 | 4.0E+06 | 1.03 |
| 59 | 10 | 2 | B | 6.5E+07 | 7.9E+07 | 1.22 |

TABLE 5-2-continued

| Example | Quaternary ammonium salt as ionic electroconductive agent | Added amount (part(s) by mass) | Evaluation of image | Initial resistivity of roller | Resistivity of roller after 10 minutes | Evaluation of change in electroconductivity |
|---|---|---|---|---|---|---|
| 60 | 16 | 2 | A | 5.3E+07 | 6.2E+07 | 1.17 |
| 61 | 10 | 2 | A | 7.8E+06 | 8.0E+06 | 1.03 |
| 62 | 16 | 2 | A | 6.2E+06 | 6.3E+06 | 1.02 |
| 63 | 1 | 2 | A | 3.6E+07 | 4.3E+07 | 1.19 |
| 64 | 6 | 2 | A | 3.7E+07 | 4.4E+07 | 1.19 |
| 65 | 10 | 2 | A | 5.2E+07 | 5.7E+07 | 1.10 |
| 66 | 14 | 2 | A | 6.0E+07 | 6.4E+07 | 1.07 |
| 67 | 16 | 2 | A | 8.5E+06 | 9.0E+06 | 1.06 |
| 68 | 19 | 2 | A | 1.2E+07 | 1.4E+07 | 1.17 |
| 69 | 21 | 2 | B | 1.5E+07 | 1.8E+07 | 1.20 |
| 70 | 22 | 2 | A | 1.3E+07 | 1.5E+07 | 1.15 |
| 71 | 16 | 0.5 | A | 1.0E+07 | 1.1E+07 | 1.10 |
| 72 | 16 | 20 | A | 3.5E+06 | 3.6E+06 | 1.03 |
| 73 | 16 | 2 | B | 3.5E+07 | 4.3E+07 | 1.23 |
| 74 | 16 | 2 | A | 6.9E+06 | 7.1E+06 | 1.03 |
| 75 | 16 | 2 | A | 5.6E+06 | 6.5E+06 | 1.16 |
| 76 | 16 | 2 | A | 6.5E+07 | 7.2E+07 | 1.11 |
| 77 | 16 | 2 | A | 8.5E+06 | 9.0E+06 | 1.06 |
| 78 | 10 | 2 | B | 7.5E+07 | 9.0E+07 | 1.20 |
| 79 | 16 | 2 | B | 6.0E+06 | 7.2E+06 | 1.20 |
| 80 | 10 | 2 | A | 8.3E+07 | 9.8E+07 | 1.18 |
| 81 | 10 | 2 | A | 3.5E+07 | 3.8E+07 | 1.09 |
| 82 | 16 | 2 | A | 2.3E+07 | 2.5E+07 | 1.09 |
| 83 | 16 | 2 | A | 3.4E+07 | 3.8E+07 | 1.12 |
| 84 | 16 | 2 | A | 1.8E+07 | 2.0E+07 | 1.11 |
| 85 | 16 | 2 | A | 2.6E+07 | 3.0E+07 | 1.15 |
| 86 | 16 | 2 | A | 3.7E+07 | 4.4E+07 | 1.19 |
| 87 | 1 | 2 | A | 6.8E+06 | 8.7E+06 | 1.28 |

TABLE 5-3

| Comparative Example | Evaluation of Image | Initial resistivity of roller (Ω) | Resistivity of roller after 10 minutes (Ω) | Evaluation of change in electroconductivity |
|---|---|---|---|---|
| 4 | C | 4.1E+07 | 5.8E+07 | 1.41 |
| 5 | D | 5.0E+07 | 7.5E+07 | 1.50 |
| 6 | C | 3.2E+07 | 4.4E+07 | 1.38 |
| 7 | D | 4.5E+07 | 6.8E+07 | 1.51 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a national phase of PCT Application No. PCT/JP2015/075775 filed Sep. 4, 2015, which claims the benefit of Japanese Patent Application No. 2014-184520, filed Sep. 10, 2014, which are both hereby incorporated by reference herein in their entirety.

REFERENCE SIGNS LIST

11 electroconductive shaft core
12 elastic layer
13 surface layer
14 intermediate layer

The invention claimed is:
1. An electroconductive member for electrophotography, comprising:
an electroconductive shaft core; and
a resin layer-comprising a binder resin and at least one quaternary ammonium salt having a structure represented by one of formulae (1) to (8):

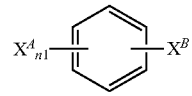
(1)

where n1 represents 2 or 3, $X^A$ represents a group having a structure represented by formula (9), and $X^B$ represents an electron-donating group or a hydrogen atom;

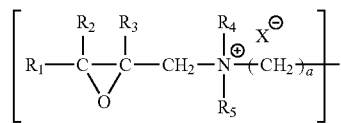
(9)

where $R_1$ to $R_3$ independently represent a hydrogen atom or a methyl group, $R_4$ and $R_5$ independently represent a methyl group, an ethyl group or a glycidyl group, $X^-$ represents an anion, and "a" represents 0 or 1;

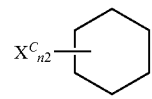
(2)

where n2 represents 2 or 3, and $X^C$ represents a group having a structure represented by formula (10);

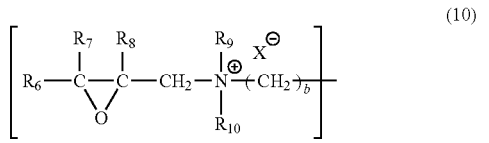

(10)

where $R_6$ to $R_8$ independently represent a hydrogen atom or a methyl group, $R_9$ and $R_{10}$ independently represent a methyl group, an ethyl group or a glycidyl group, $X^-$ represents an anion, and "b" represents 0 or 1;

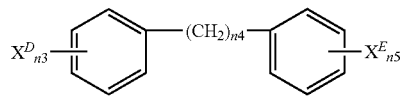

(3)

where n3 and n5 independently represent 1 or 2, n4 represents 1 or 2, and $X^D$ and $X^E$ independently represent a group having a structure represented by formula (11);

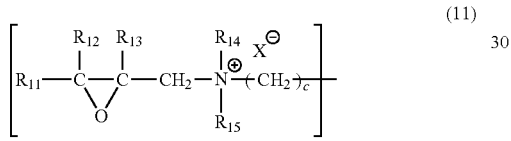

(11)

where $R_{11}$ to $R_{13}$ independently represent a hydrogen atom or a methyl group, $R_{14}$ and $R_{15}$ independently represent a methyl group, an ethyl group or a glycidyl group, $X^-$ represents an anion, and "c" represents 0 or 1;

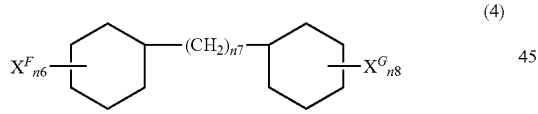

(4)

where n6 and n8 independently represent 1 or 2, n7 represents 1 or 2, and $X^F$ and $X^G$ independently represent a group having a structure represented by formula (12);

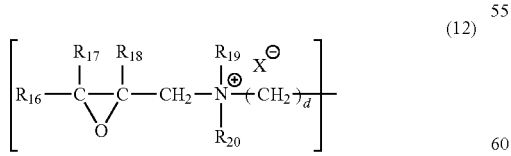

(12)

where $R_{16}$ to $R_{18}$ independently represent a hydrogen atom or a methyl group, $R_{19}$ and $R_{20}$ independently represent a methyl group, an ethyl group or a glycidyl group, $X^-$ represents an anion, and "d" represents 0 or 1;

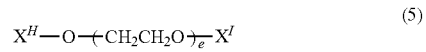

(5)

where "e" represents 1 or 2, and $X^H$ and $X^I$ independently represent a group having a structure represented by formula (13);

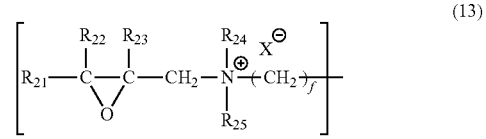

(13)

where $R_{21}$ to $R_{23}$ independently represent a hydrogen atom or a methyl group, $R_{24}$ and $R_{25}$ independently represent a methyl group, an ethyl group or a glycidyl group, $X^-$ represents an anion, and "f" represents 2 or 3;

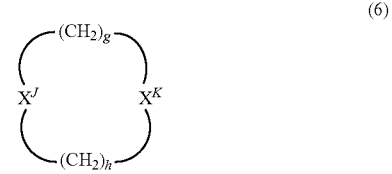

(6)

where "g" and "h" independently represent 2 or 3, and $X^J$ and $X^K$ independently represent a group having a structure represented by formula (14);

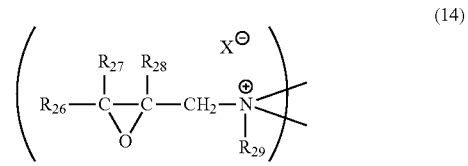

(14)

where $R_{26}$ to $R_{28}$ independently represent a hydrogen atom or a methyl group, $R_{29}$ represents a methyl group, an ethyl group or a glycidyl group, and $X^-$ represents an anion;

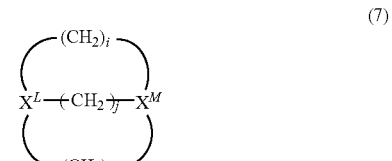

(7)

where "i", "j", and "k" independently represent 2 or 3, and $X^L$ and $X^M$ independently represent a group having a structure represented by formula (15);

(15)

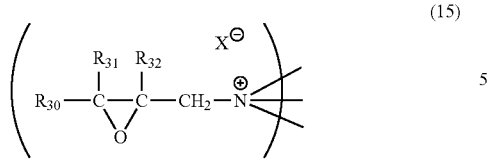

where $R_{30}$ to $R_{32}$ independently represent a hydrogen atom or a methyl group, and $X^-$ represents an anion;

(8)

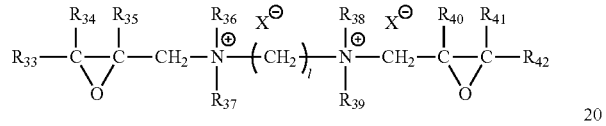

where $R_{33}$ to $R_{35}$ and $R_{40}$ to $R_{42}$ independently represent a hydrogen atom or a methyl group, $R_{36}$ to $R_{39}$ independently represent a methyl group, an ethyl group or a glycidyl group, "l" represents an integer of 2 to 12, and $X^-$ represents an anion.

2. An electroconductive member for electrophotography, comprising:

an electroconductive shaft core; and a resin layer comprising a binder resin to which a quaternary ammonium salt is fixed, the binder resin being obtained from (i) a compound having at least two functional groups selected from the group consisting of a hydroxyl group, a mercapto group, an amino group and an acid anhydride group, and (ii) at least one quaternary ammonium salt having a structure represented by one of formulae (1) to (8), said quaternary ammonium salt being fixed by a reaction between the functional group in compound (i) and an epoxy group in quaternary ammonium salt (ii):

(1)

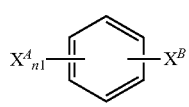

where n1 represents 2 or 3, $X^A$ represents a group having a structure represented by formula (9), and $X^B$ represents an electron-donating group or a hydrogen atom;

(9)

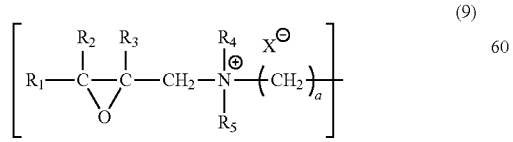

where $R_1$ to $R_3$ independently represent a hydrogen atom or a methyl group, $R_4$ and $R_5$ independently represent a methyl group, an ethyl group or a glycidyl group, $X^-$ represents an anion, and "a" represents 0 or 1;

(2)

where n2 represents 2 or 3, and $X^C$ represents a group having a structure represented by formula (10);

(10)

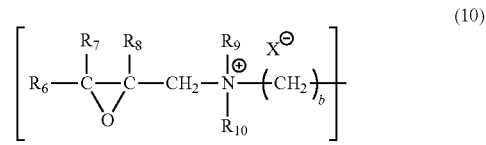

where $R_6$ to $R_8$ independently represent a hydrogen atom or a methyl group, $R_9$ and $R_{10}$ independently represent a methyl group, an ethyl group or a glycidyl group, $X^-$ represents an anion, and "b" represents 0 or 1;

(3)

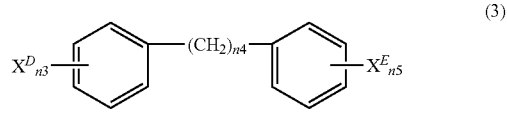

where n3 and n5 independently represent 1 or 2, n4 represents 1 or 2, and $X^D$ and $X^E$ independently represent a group having a structure represented by formula (11);

(11)

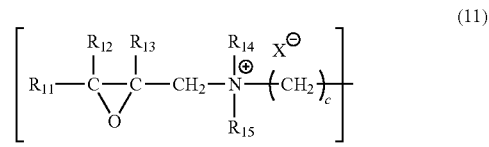

where $R_{11}$ to $R_{13}$ independently represent a hydrogen atom or a methyl group, $R_{14}$ and $R_{15}$ independently represent a methyl group, an ethyl group or a glycidyl group, $X^-$ represents an anion, and "c" represents 0 or 1;

(4)

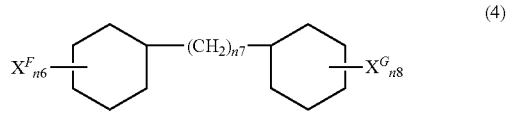

where n6 and n8 independently represent 1 or 2, n7 represents 1 or 2, and $X^F$ and $X^G$ independently represent a group having a structure represented by formula (12);

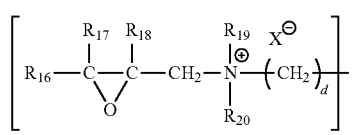
(12)

where $R_{16}$ to $R_{18}$ independently represent a hydrogen atom or a methyl group, $R_{19}$ and $R_{20}$ independently represent a methyl group, an ethyl group or a glycidyl group, $X^-$ represents an anion, and "d" represents 0 or 1;

(5)

where "e" represents 1 or 2, and $X^H$ and $X^I$ independently represent a group having a structure represented by formula (13);

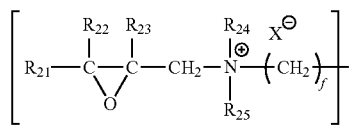
(13)

where $R_{21}$ to $R_{23}$ independently represent a hydrogen atom or a methyl group, $R_{24}$ and $R_{25}$ independently represent a methyl group, an ethyl group or a glycidyl group, $X^-$ represents an anion, and "f" represents 2 or 3;

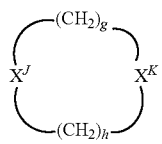
(6)

where "g" and "h" independently represent 2 or 3, and $X^J$ and $X^K$ independently represent a group having a structure represented by formula (14);

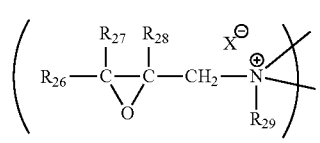
(14)

where $R_{26}$ to $R_{28}$ independently represent a hydrogen atom or a methyl group, $R_{29}$ represents a methyl group, an ethyl group or a glycidyl group, and $X^-$ represents an anion;

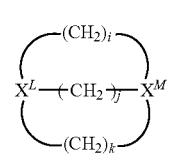
(7)

where "i", "j", and "k" independently represent 2 or 3, and $X^L$ and $X^M$ independently represent a group having a structure represented by formula (15);

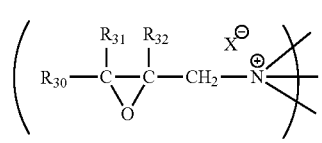
(15)

where $R_{30}$ to $R_{32}$ independently represent a hydrogen atom or a methyl group, and $X^-$ represents an anion;

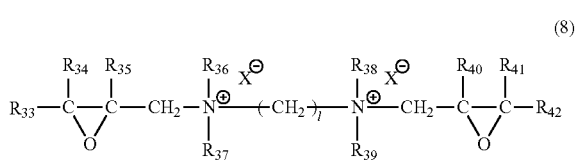
(8)

where $R_{33}$ to $R_{35}$ and $R_{40}$ to $R_{42}$ independently represent a hydrogen atom or a methyl group, $R_{36}$ to $R_{39}$ independently represent a methyl group, an ethyl group or a glycidyl group, "l" represents an integer of 2 to 12, and $X^-$ represents an anion.

3. An electroconductive member for electrophotography according to claim 2, wherein the compound having two or more functional groups has an ethylene oxide structure.

4. A process cartridge, which is removably mounted onto a main body of an electrophotographic image forming apparatus, the process cartridge comprising the electroconductive member for electrophotography according to claim 3.

5. A process cartridge according to claim 4, wherein the process cartridge comprises the electroconductive member for electrophotography as at least one of a charging roller or a developing roller.

6. An electrophotographic image forming apparatus, comprising the electroconductive member for electrophotography according to claim 3.

7. A process cartridge, which is removably mounted onto a main body of an electrophotographic image forming apparatus, the process cartridge comprising the electroconductive member for electrophotography according to claim 3.

8. A process cartridge according to claim 7, wherein the electroconductive member for electrophotography is at least one of a charging roller or a developing roller.

9. An electrophotographic image forming apparatus, comprising the electroconductive member for electrophotography according to claim 3.

10. A process cartridge, which is removably mounted onto a main body of an electrophotographic image forming apparatus, the process cartridge comprising the electroconductive member for electrophotography according to claim 2.

11. A process cartridge according to claim 10, wherein the electroconductive member for electrophotography is at least one of a charging roller or a developing roller.

12. An electrophotographic image forming apparatus, comprising the electroconductive member for electrophotography according to claim 2.

13. A process cartridge, which is removably mounted onto a main body of an electrophotographic image forming apparatus, the process cartridge comprising the electroconductive member for electrophotography according to claim 1.

14. A process cartridge according to claim 13, wherein the electroconductive member for electrophotography is at least one of a charging roller or a developing roller.

15. An electrophotographic image forming apparatus, comprising the electroconductive member for electrophotography according to claim 1.

* * * * *